United States Patent
Singh et al.

(10) Patent No.: US 11,339,126 B2
(45) Date of Patent: May 24, 2022

(54) COMPOUNDS FOR THE REDUCING LIPOTOXIC DAMAGE

(71) Applicant: Mayo Foundation for Medical Education and Research, Rochester, MN (US)

(72) Inventors: Vijay P. Singh, Scottsdale, AZ (US); Sampath-Kumar Anandan, Fremont, CA (US); Kevin Greenman, Sunnyvale, CA (US); Zeeshan Kamal, Milpitas, CA (US)

(73) Assignees: Mayo Foundation for Medical Education and Research, Rochester, MN (US); Nanosyn, Inc., Santa Clara, CA (US)

( * ) Notice: Subject to any disclaimer, the term of this patent is extended or adjusted under 35 U.S.C. 154(b) by 0 days.

(21) Appl. No.: 16/629,842

(22) PCT Filed: Jul. 12, 2018

(86) PCT No.: PCT/US2018/041796
§ 371 (c)(1),
(2) Date: Jan. 9, 2020

(87) PCT Pub. No.: WO2019/014434
PCT Pub. Date: Jan. 17, 2019

(65) Prior Publication Data
US 2021/0139421 A1  May 13, 2021

Related U.S. Application Data

(60) Provisional application No. 62/531,454, filed on Jul. 12, 2017.

(51) Int. Cl.
*A61K 31/365* (2006.01)
*C07D 205/08* (2006.01)
*A61P 3/04* (2006.01)

(52) U.S. Cl.
CPC .............. *C07D 205/08* (2013.01); *A61P 3/04* (2018.01)

(58) Field of Classification Search
CPC .......... C07D 205/08; A61P 3/04; A61P 17/02; A61P 17/10; A61P 31/00; A61P 1/18; A61K 31/365
(Continued)

(56) References Cited

U.S. PATENT DOCUMENTS 4,931,463 A  6/1990  Barbier et al.
6,432,400 B1  8/2002  Chapus
(Continued)

FOREIGN PATENT DOCUMENTS

CN  85108888  7/1986
EA  15940  12/2011
(Continued)

OTHER PUBLICATIONS

Asenn et al. Acute pancreatitis following orlistat therapy: report of two cases. Journal of the pancreas. Abstract. vol. 11, No. 1, pp. 61-63, Jan. 2010. (Year: 2010).
(Continued)

*Primary Examiner* — Taylor V Oh
(74) *Attorney, Agent, or Firm* — Fish & Richardson P.C.

(57) ABSTRACT

Provided herein are novel lipase inhibitors and methods for using the same to treat inflammation, multisystem organ failure, necrotic pancreatic acinar cell death, acute pancreatitis, sepsis (e.g., culture negative sepsis), burns, and acne. For example, provided herein are two novel lipase inhibitors useful in the methods described herein:

(Continued)

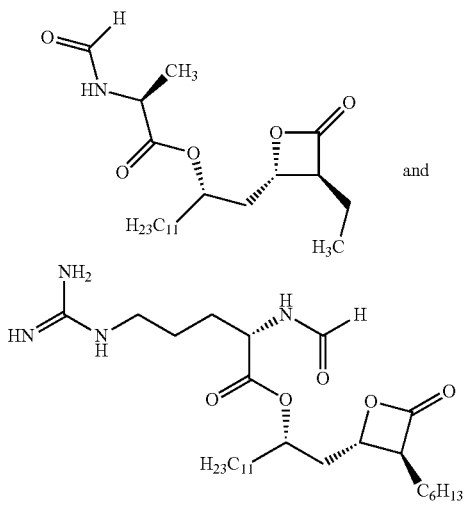

or a pharmaceutically acceptable salt thereof.

15 Claims, 31 Drawing Sheets

(58) Field of Classification Search
USPC .......................................................... 514/183
See application file for complete search history.

(56) References Cited

U.S. PATENT DOCUMENTS

| | | |
|---|---|---|
| 9,023,887 B2 | 5/2015 | Singh |
| 2004/0018197 A1 | 1/2004 | Stafford et al. |
| 2009/0124681 A1 | 5/2009 | Smith et al. |
| 2011/0195114 A1 | 8/2011 | Carrara et al. |
| 2012/0289588 A1 | 11/2012 | Singh |
| 2015/0099800 A1 | 4/2015 | Duclos, Jr. |
| 2015/0283109 A1 | 10/2015 | Singh |
| 2018/0319894 A1 | 11/2018 | Singh |
| 2020/0385489 A1 | 12/2020 | Singh |

FOREIGN PATENT DOCUMENTS

| | | |
|---|---|---|
| RU | 2471790 | 1/2013 |
| WO | WO 1998/017807 | 4/1998 |

OTHER PUBLICATIONS

Banks et al., "Classification of acute pancreatitis—2012: revision of the Atlanta classification and definitions by international consensus," Gut, 62:102-11, Jan. 2013.
Chan et al. Acute Pancreatitis Animal Models and Recent Advances in Basic Research, Pancreas vol. 34:1-14, 2007, (Year: 2007).
GBD 2013 Mortality and Causes of Death Collaborators, "Global, regional, and national age-sex specific all-cause and cause-specific mortality for 240 causes of death, 1990-2013: a systematic analysis for the Global Burden of Disease Study 2013," Lancet, Dec. 2014, 385(9963): 117-71.
International Preliminary Report on Patentability in International Application No. PCT/US2018/041796 dated Jan. 14, 2020, 9 pages.
International Search Report & Written Opinion in International Application No. PCT/US2018/041796 dated Nov. 29, 2018, 28 pages.
Kocieński et al., "Asymmetric syntheses of panclicins A-E via [2+2] cycloaddition of alkyl (trimethyl silyl) ketenes to a β-silyloxyaldehyde,"
Journal of the Chemical Society, Perkin Transactions 1. 1998(8):1373-82.
Lankisch et al., "Acute pancreatitis," Lancet, Jul. 2015, 386(9988):85-96.
Lee et al., "Elevated amylase and lipase levels in the neurosurgery intensive care unit," J. Chin, Med. Assoc., 73(1):8-14, Jan. 2010,.
Levitt et al. "Chapter 32: Diagnosis of Acute Pancreatitis," The Pancreas: Biology, Pathophysiology, and Disease, 2nd Ed. Dec. 31, 1993 (Dec. 31, 1993), Raven Press, NY, pp. 613-635.(Dec. 31, 1993). Retrieved from the Internet: <http://journals.lww.com/pancreasjournal/Documents/pancreas%20chapters/the%20pancreas% 20Ch32.pdf> on Dec. 15, 2016 (Dec. 15, 2016). entire document.
Malecki et al. Therapeutic Administration of Orlistat, Rosiglitazone, or the Chennokine Receptor Antagonist R5102895 Fails to Improve the Severity of Acute Pancreatitis in Obese Mice. Pancreas vol. 43:903-908, 2014 (Year: 2014).
Malinoski et al., "Elevated serum pancreatic enzyme levels after hemorrhagic shock predict organ failure and death," J. Trauma, Sep. 2009.
Manjuck et al., "Clinical significance of increased lipase levels on admission to the ICU," Chest, 127(1):246-50, Jan. 2005.
Muniraj et al., "Chronic pancreatitis, a comprehensive review and update. Part I: epidemiology, etiology, risk factors, genetics, pathophysiology, and clinical features," Dis. Mon,, Dec. 2014, 60(12):530-50.
Munoz et al., "Diagnosis and management of acute pancreatitis," Am. Fam. Physician, Jul. 2000, 62(1): 164-74.
Murat et al. An Unexpected Result of Obesity Treatment: Orlistat-Related Acute Pancreatitis. Case reports in gastroenterology, Abstract. vol. 9, No. 2, pp. 152-155 (May-Aug. 2015). Electronic Publication Date: May 8, 2015 (Year: 2015).
Navina et al., "Lipotoxicity causes multisystem organ failure and exacerbates acute pancreatitis in obesity," Sci. Transl. Med., Nov. 2011.
Paul, W. E. Fundamental Immunology, Third Edition Textbook, "Fv Structure and Diversity in Three Dimensions" pp. 292-295; Raven Press, New York; 1993. (Year: 1993).
Rifai et al. The tripeptide analog feG ameliorates severity of acute pancreatitis in a caerulein mouse model. Am J Physiol Gastrointest Liver Physiol 294: G1094-G1099, 2008, (Year: 2008).
Ryan et al., "Postburn pancreatitis," Ann. Surg., 222(2): 163-170, Aug. 1995.
Subramanian et al., "Association between the pancreatic enzyme level and organ failure in trauma patients," Trauma Mon,, 21(2):e20773, May 2016.
Wilen et al., "Strategies in optical resolutions," Tetrahedron, 33(21):2725-36, Jan. 1977.
U.S. Appl. No. 15/773,450, filed May 3, 2018, Vijay P. Singh, Published.
EP Extended Search Report in European Application No. 18831486.8, dated Apr. 6, 2021, 5 pages.
Johnston et al., "Assay and inhibition of diacylglycerol lipase activity," Bioorg. Med. Chem. Letters, Jul. 2012, 22(14):4584-4592.
U.S. Appl. No. 17/002,665, filed Aug. 25, 2020, Vijay P. Singh, Published.
Emmerich et al., "Human Lipoprotein Lipas: Analysis of the Catalytic Triad by Site-Directed Mutagenesis of SER-132, ASP-156, and HIS-241," J. Biol. Chemistry, Feb. 25, 1992, 267(6):4161-4165.
Ortar et al., "Tetrahydrolipstatin Analogues as Modulators of Endocannabinoid 2-Arachidonoylglycerol Metabolism," J. Med. Chemistry, Oct. 3, 2008, 51(21):6970-6979.
Patel et al., "Lipolysis of visceral adipocyte triglyceride by pancreatic lipases converts mild acute pancreatitis to severe pancreatitis independent of necrosis and inflammation," Am. J. Pathology, Mar. 2015, 185(3): 808-819.
Pleiss et al., "Anatomy of lipase binding sites: the seissile fatty acid binding site," Chem. Phys. Lipids, Jun. 1998, 93(1-2):67-80.
Richardson et al., "Synthesis of Novel β-Lactone Inhibitors of Fatty Acid Synthase," J. Med. Chemistry, Aug. 19, 2008, 51(17):5285-5296.

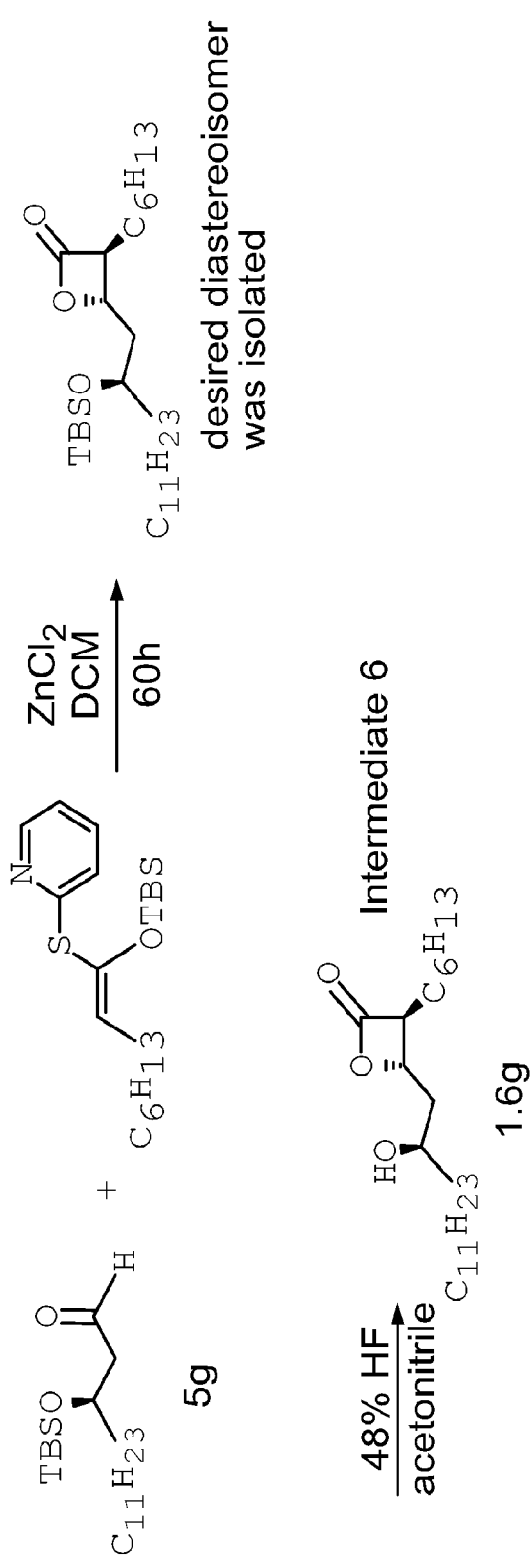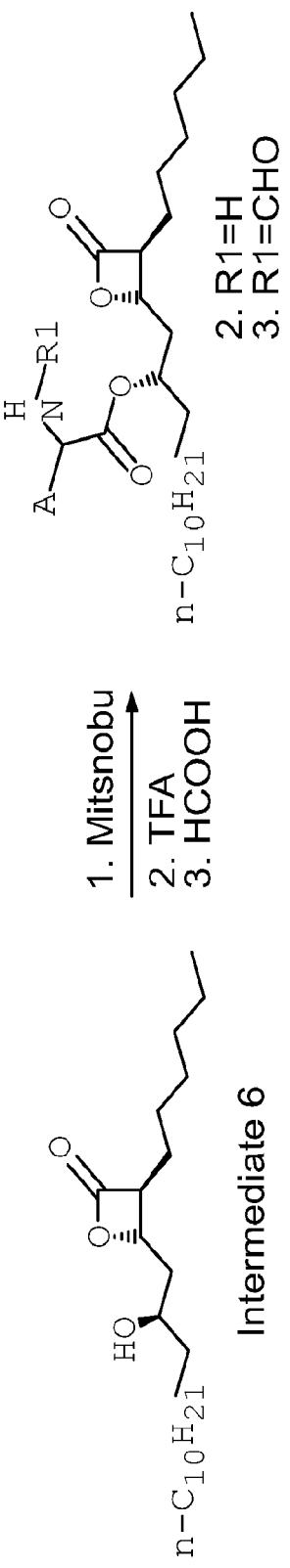
FIG. 2

Non-formyl groups were substituted as:
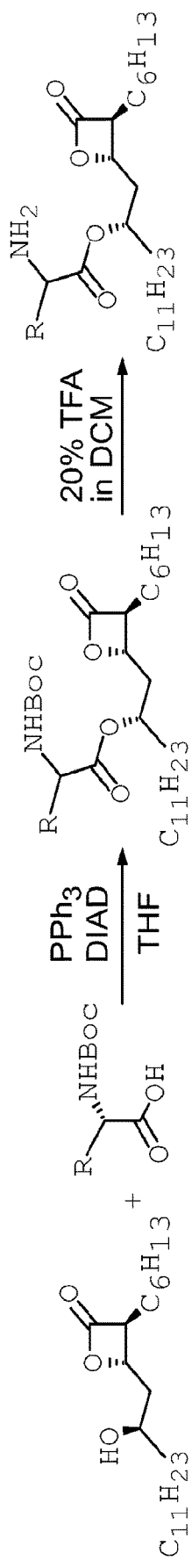
Formyl groups were substituded as (For details see next page)
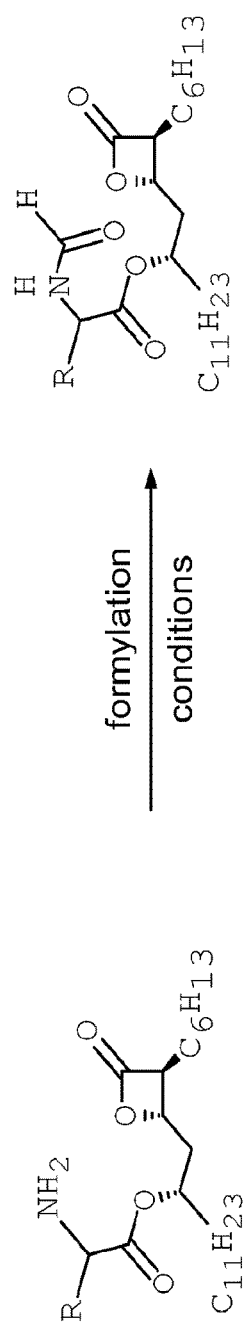
FIG. 2 Cont.

| % descrease in ATP over control acini | | | | | | | | | |
|---|---|---|---|---|---|---|---|---|---|
| Dose (uM) | Orli | 767 | 743 | 742 | 741 | 740 | 739 | 734 | 733 | 762 |
| 200 | 9.14 | 4.24 | 57.37 | 38.66 | 3.04 | 9.30 | 10.87 | 23.43 | 17.48 | 10.11 |
| 66.6 | 3.02 | -9.59 | 51.86 | 0.10 | 4.60 | -9.08 | -0.24 | 5.45 | 10.80 | 6.92 |
| 22.2 | 1.66 | -13.61 | 30.21 | 5.33 | 1.03 | -6.36 | 0.11 | 4.56 | 8.31 | 6.54 |
| 7.4 | 3.48 | -6.32 | 4.72 | 9.30 | -2.40 | -0.40 | 2.39 | 8.15 | 6.50 | 4.13 |

| increase in LDH leakage over 4 hours over controls (19.6%) | | | | | | | | | |
|---|---|---|---|---|---|---|---|---|---|
| Dose (uM) | Orli | 767 | 743 | 742 | 741 | 740 | 739 | 734 | 733 | 762 |
| 200 | 13.35 | 10.97 | 70.92 | 34.52 | -7.81 | -12.02 | 7.81 | 8.39 | -6.35 | -5.94 |
| 66.6 | 10.81 | -2.72 | 60.33 | -8.76 | -7.54 | -14.47 | -4.38 | -14.16 | -13.99 | -9.33 |
| 22.2 | 11.02 | 0.48 | 26.74 | 9.28 | -4.66 | -15.61 | 7.50 | -9.15 | -6.38 | -3.73 |
| 7.4 | 1.88 | 2.57 | -2.46 | 19.06 | -1.88 | -5.78 | 30.60 | 1.25 | 1.88 | 0.88 |

FIG. 19

| Agent | hPTLIC50 µM Fresh | hPTLIC50 µM overnight | hPLRP2 IC50 µM | hCEL IC50 µM | LDH leak at 20xIC50 | ATP drop at 20xIC50 |
|---|---|---|---|---|---|---|
| 733 | 0.5 | 5.5(11x) | 0.07 | 0.1 | 1.9% | 8.3% |
| *767* | 0.55 | 1.1(2x) | <0.03 | 1.5 | 0.5% | 0% |
| 740 | 0.7 | 1.05(2x) | 0.15 | 0.1 | 0% ?? | 0% |
| 734 | 1 | 11(11x) | <0.03 | 0.1 | 0% ?? | 4.5% |
| 739 | 2 | 38(19x) | 0.3 | 0.1 | 8% | 0% |
| 741 | 7 | 35(5x) | 0.7 | 0.35 | 0% (??) | 3% |
| orlistat | 9 | 60(7x) | 5 | 10 | 13.3% | 9% |

FIG. 21

Orlistat has 80% efficacy in reducing mortality in severe pancreatitis. If is used as 50 mg/kg/dose, BID, and administered over 2 days. The first dose was given 2 hours after the initiation of pancreatitis Use of orlistat at this schedule is complicated by hypertriglyceridemia.

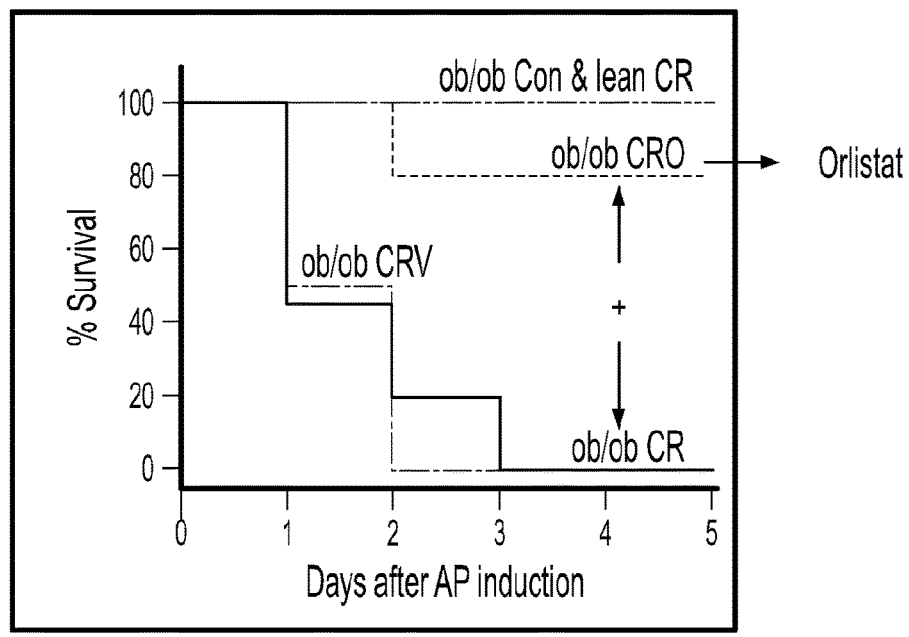

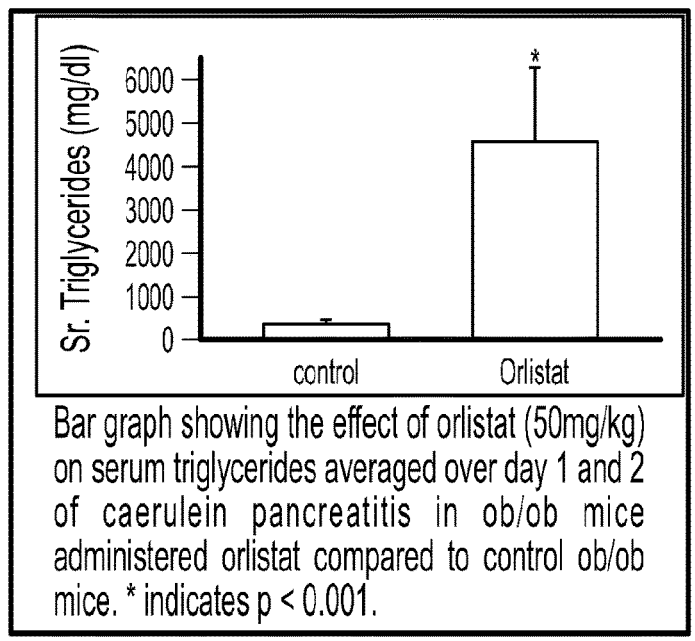

Bar graph showing the effect of orlistat (50mg/kg) on serum triglycerides averaged over day 1 and 2 of caerulein pancreatitis in ob/ob mice administered orlistat compared to control ob/ob mice. * indicates $p < 0.001$.

FIG. 22

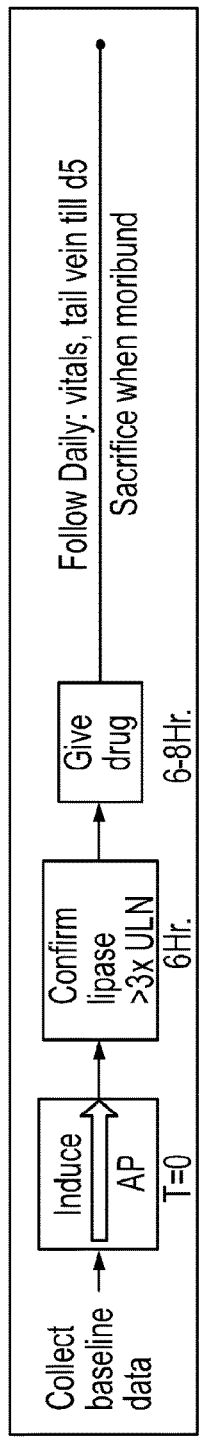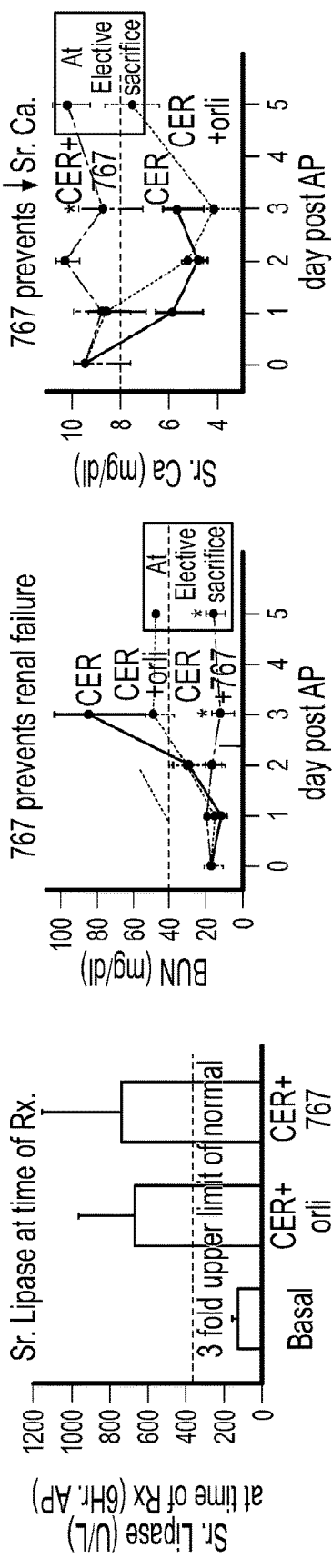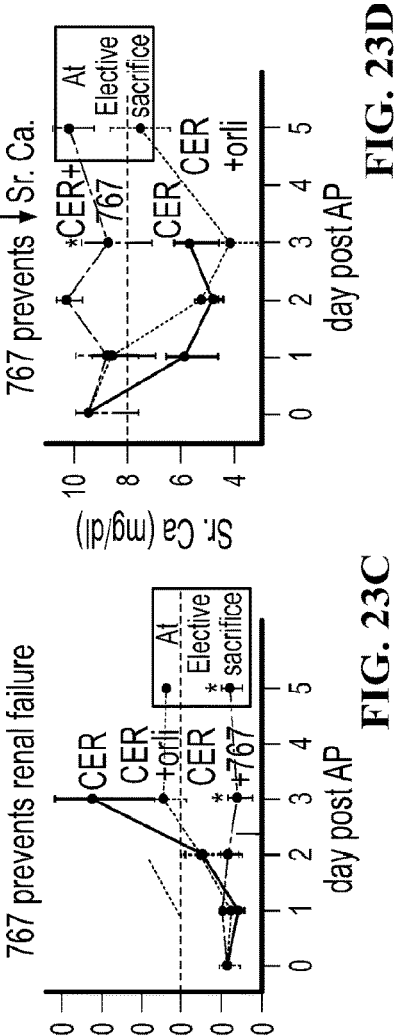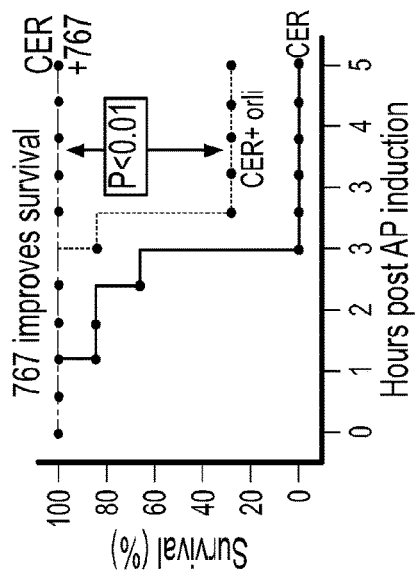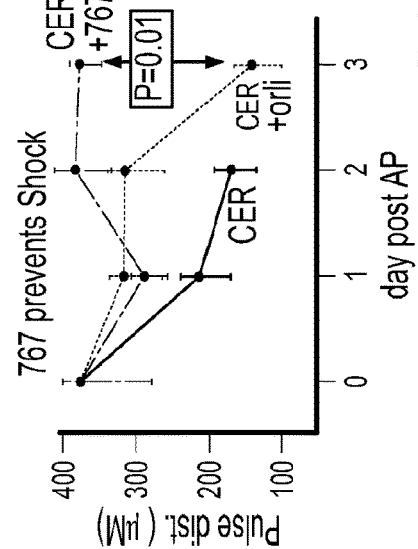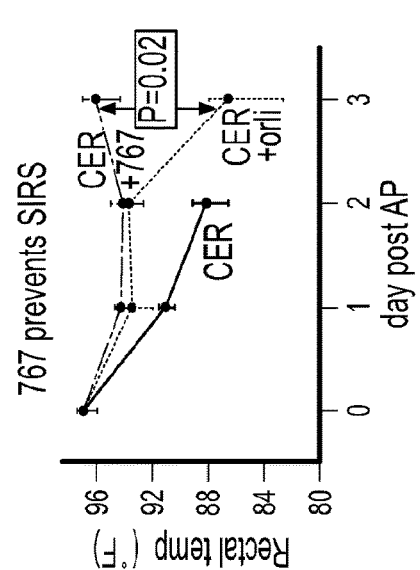
FIG. 23A  FIG. 23B  FIG. 23C  FIG. 23D  FIG. 23E  FIG. 23F  FIG. 23G

| Parameter | orlistat | 767 |
|---|---|---|
| Effective Dosing schedule | 2/day x 3 day -repeated dosing | Single dose |
| Dose | 50mg/kg/dose | 20 mg/kg |
| Stability in aqueous environment for 24 hours | Unstable- requires fresh formulation | Stable |
| Vehicle | • Liposomal- Harmful?<br>• Phospholipases cleave phospholipid→lipotoxic Fatty acids<br>• TG emulsion<br>• Cyclodextrins are ineffective | 0.3% ethanol. 767 makes its own micelles |
| Complication | Hypertriglyceridemia > 5000 | Triglycerides <500. |
| Mortality | 20% at high repeated dose, 71% (5/7) at 20mg/kg | 0% (0/8) at 5 days |
| SIRS: WBC counts < 4000/mm$^3$ | As a Single 20 mg/kg dose — 4/7 | 0/8 |
| SIRS: Hypothermia (Temp < 93F) | As a Single 20 mg/kg dose — 7/7 | 0/8 |
| MSOF: Shock (pulse distention <50%) | As a Single 20 mg/kg dose — 7/7 | 0/8 |
| MSOF: Renal failure (BUN > 40 mg/dl) | As a Single 20 mg/kg dose — 7/7 | 0/8 |

SIRS: Systemic inflammatory response syndrome. MSOF: Multi-system organ failure

FIG. 25

Color of spirit blue agar with P acnes grown for 6 days under anaerobic conditions

COMPOUNDS FOR THE REDUCING LIPOTOXIC DAMAGE

CROSS-REFERENCE TO RELATED APPLICATIONS

This application is a National Stage application under 35 U.S.C. § 371 of International Application No. PCT/US2018/041796, having an International Filing Date of Jul. 12, 2018, which claims priority to U.S. Provisional Application Ser. No. 62/531,454, filed on Jul. 12, 2017, the contents of which are incorporated by reference in their entirety.

TECHNICAL FIELD

The present disclosure relates to the use of lipase inhibitors for the treatment of severe pancreatitis and/or acne.

BACKGROUND

The pancreas produces enzymes that aid in digestion and absorption of food; one such enzyme is lipase, which digests fat. Certain individuals (e.g., obese individuals) have an increased risk of developing multisystem organ failure in acute inflammatory conditions such as severe burns, severe trauma, critical illness, and acute pancreatitis (AP). Pancreatitis is associated with the release of destructive digestive enzymes from pancreatic acinar cells into the pancreas itself. When AP is initiated, it can quickly become severe AP (SAP). This is a concern because SAP results in 40 to 50% mortality when complicated by acute renal failure, respiratory failure, hypocalcemia, and other manifestations of multisystem organ failure or by large areas of pancreatic necrosis. With no effective therapies, the current management standard is supportive care and managing complications when they occur.

SUMMARY

Provided herein are novel lipase inhibitors and methods for using the same to treat pancreatitis and/or organ failure and/or acne comprising administering, to a subject in need of such treatment, an effective amount of a lipase inhibitor as provided herein. The methods provided herein are based, at least in part, on the discoveries that lipotoxicity contributes to inflammation, multisystem organ failure, necrotic pancreatic acinar cell death, acute pancreatitis, sepsis (e.g., culture negative sepsis), burns, acne, and infections, and that inhibition of lipase activity is able to reduce indices associated with these conditions. Accordingly, in some embodiments, provided herein are methods and compositions for limiting lipotoxicity and thereby reducing the likelihood of poor outcomes associated with acute pancreatitis and other severe systemic conditions.

Provided herein is a compound selected from the group consisting of:

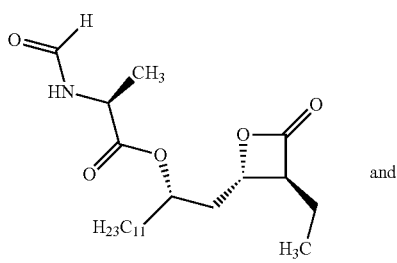
and

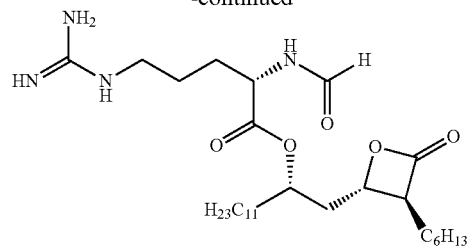

or a pharmaceutically acceptable salt thereof. In some embodiments, the compound is:

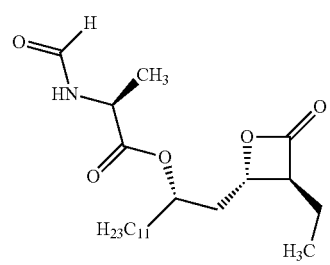

or a pharmaceutically acceptable salt thereof. In some embodiments, the compound is:

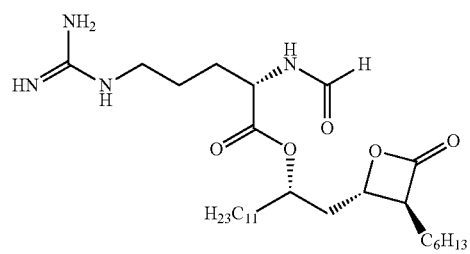

or a pharmaceutically acceptable salt thereof.

Further provided herein is a pharmaceutical composition comprising one or more of the compounds provided herein and a pharmaceutically acceptable excipient.

This disclosure also provides methods of treating acute pancreatitis in a subject in need thereof, the method comprising administering to the subject a therapeutically effective amount of a compound provided herein or a pharmaceutically acceptable salt thereof. In some embodiments, the acute pancreatitis is severe. In some embodiments, the acute pancreatitis is downgraded from severe to mild following administration. In some embodiments, the subject is obese. In some embodiments, the risk of developing shock, renal failure, and/or pulmonary failure is reduced.

Also provided herein is a method of treating acne in a subject in need thereof, the method comprising administering to the subject a therapeutically effective amount of a compound provided herein or a pharmaceutically acceptable salt thereof.

Further provided herein is a method of treating sepsis in a subject in need thereof, the method comprising administering to the subject a therapeutically effective amount of a compound provided herein or a pharmaceutically acceptable salt thereof. In some embodiments, the sepsis is culture negative sepsis.

This disclosure also provides methods of treating burns in a subject in need thereof, the method comprising administering to the subject a therapeutically effective amount of a compound provided herein or a pharmaceutically acceptable salt thereof.

Also provided herein is a method for treating infections in a subject in need thereof, the method comprising administering to the subject a therapeutically effective amount of a compound provided herein or a pharmaceutically acceptable salt thereof. In some embodiments, the infection is caused by one or more organisms selected from the group consisting of *P. auregenosa*, *S. aureus*, *B. subtilis*, and *B. cepecia*.

In some of the above embodiments, the compound is:

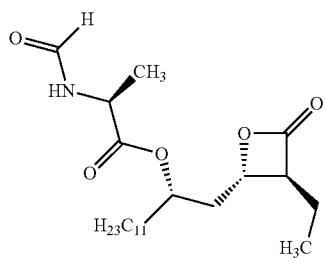

or a pharmaceutically acceptable salt thereof. In some embodiments of the above embodiments, the compound is:

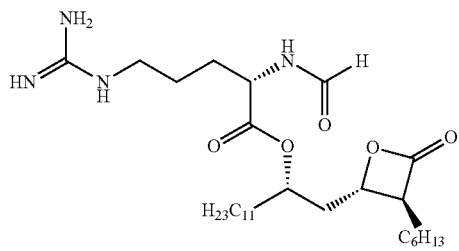

or a pharmaceutically acceptable salt thereof.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 2 is a scheme detailing a synthetic route to prepare amino-ester modifications to the orlistat core.

FIG. 19 shows tables of values obtained from toxicity studies in mouse pancreatic cells.

FIG. 21 provides a tabular summary of the in vitro studies described herein.

FIG. 22 provides a summary of the use of orlistat in reducing severe pancreatitis.

FIG. 23 provides the results of in vivo testing of compound 767. FIG. 23A provides the study timeline; FIG. 23B provides a bar graph of the serum lipase concentration; FIG. 23C provides a graph showing serum blood urea nitrogen levels at various time points; FIG. 23D provides a graph showing serum calcium levels at various time points; and FIG. 23E provides a graph showing protection against systemic inflammatory response syndrome (SIRS); FIG. 23F provides a graph showing protection against shock and FIG. 23G provides a graph showing improved survival FIG. 24 provides photographs of treated mice.

FIG. 25 provides a tabular summary of the in vivo studies with compound 767 and orlistat.

DETAILED DESCRIPTION

Figure 1:
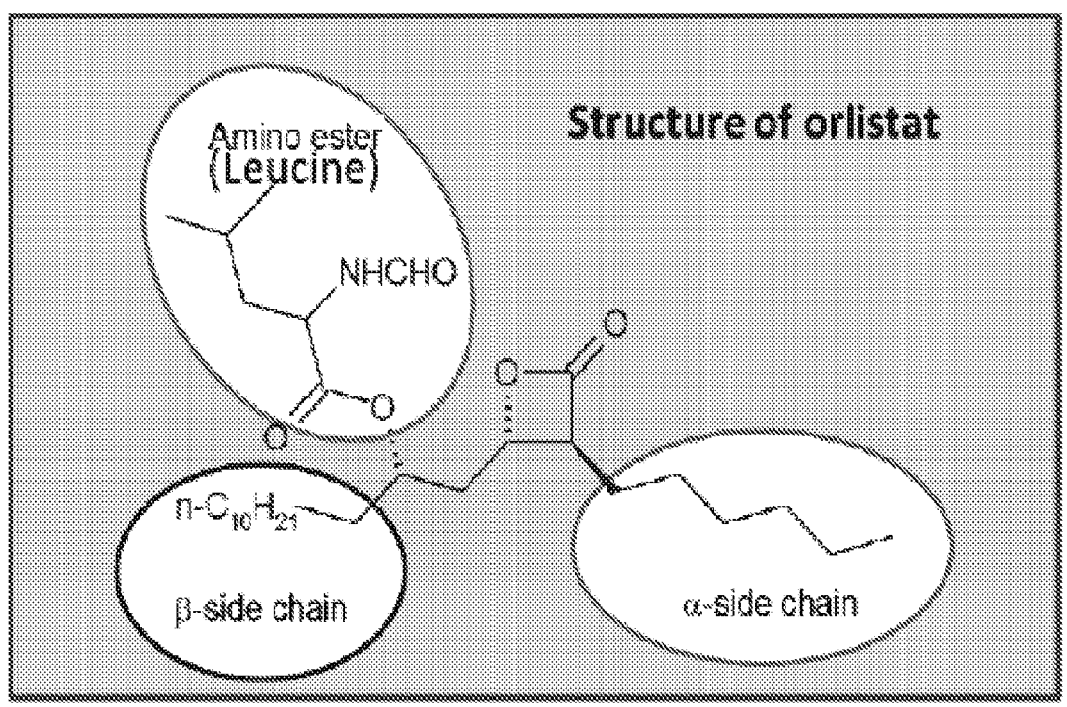
FIG. 1 is a schematic of the structure of orlistat dividing the compound into three main regions.

Presently, severe pancreatitis is often treated through administration of the FDA approved lipase inhibitor, orlistat. While lipase inhibition reduces the severity of pancreatitis, the use of orlistat is complicated by the need of repeated dosing (e.g., 50 mg/kg BID for two days) during pancreatitis, and the hypertriglyceridemia associated with the use of this compound. Provided herein are compounds that provide therapeutic benefits in pancreatitis, without the need of repeated dosing or the complications associated with orlistat.

Compounds provided herein include those described in Table 1.

TABLE 1

| Compound Number | Structure |
| --- | --- |
| 728 | (structure shown) |
| 731 | (structure shown) |
| 729 | (structure shown) |

TABLE 1-continued
| Compound Number | Structure |
|---|---|
| 727 | 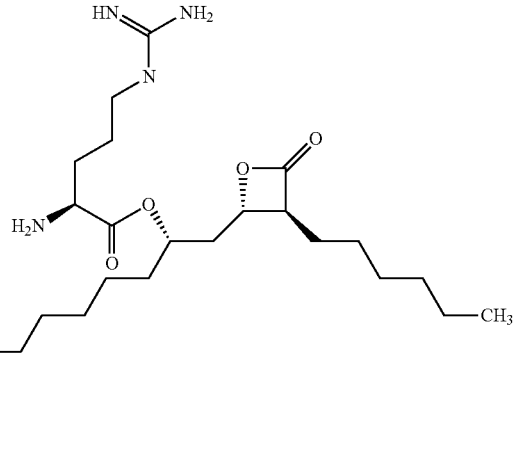 |
| 725 | 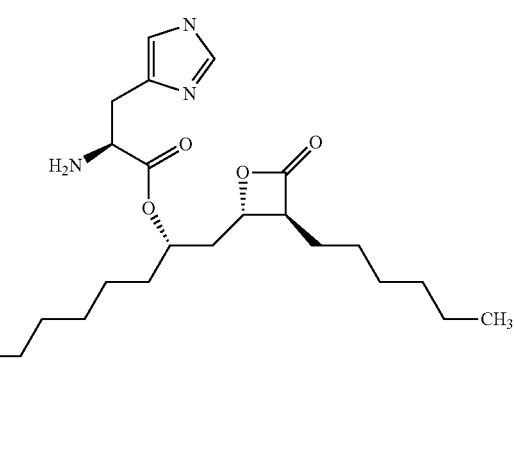 |
| 716 | 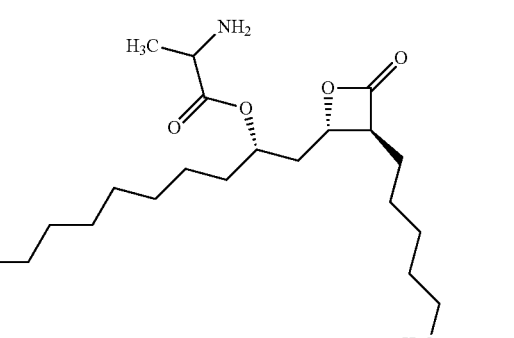 |

TABLE 1-continued
| Compound Number | Structure |
|---|---|
| 718 | 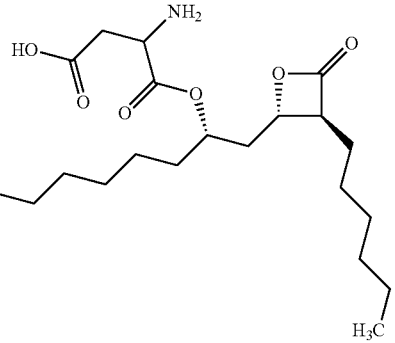 |
| 717 | 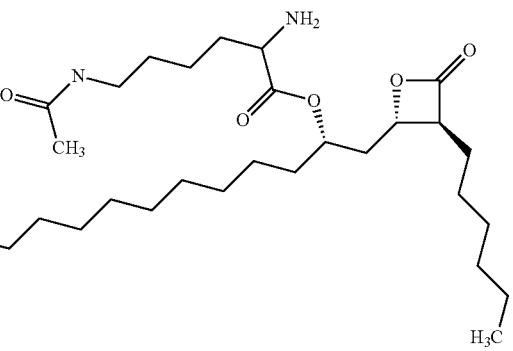 |
| 726 | 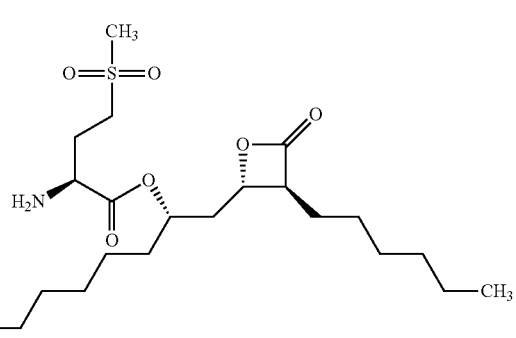 |
| 724 | 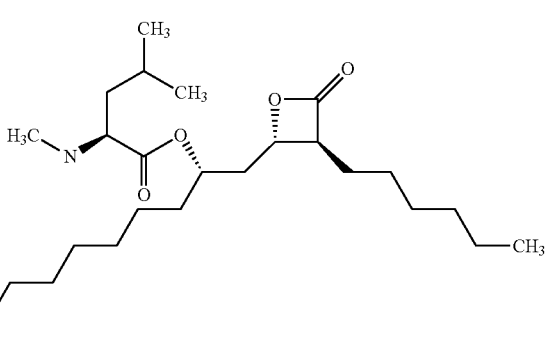 |

TABLE 1-continued
| Compound Number | Structure |
|---|---|
| 732 | 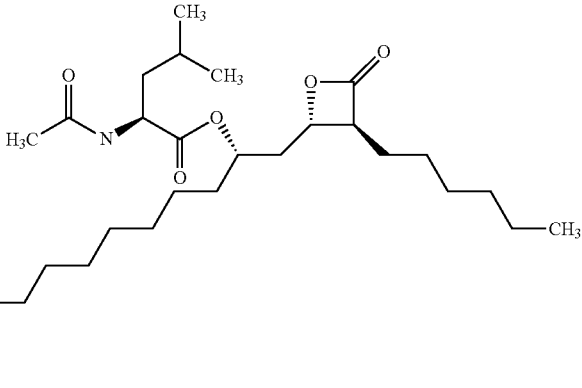 |
| 733 | 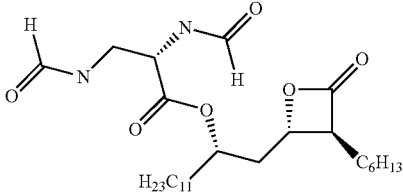 |
| 734 | 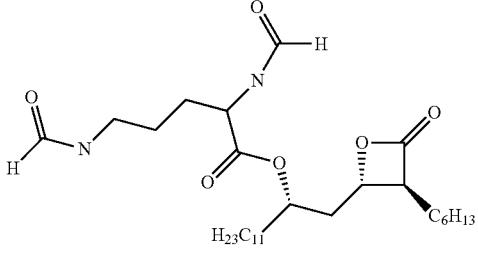 |
| 738 | 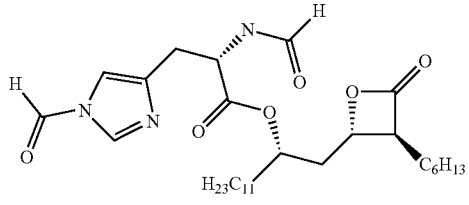 |
| 736 | 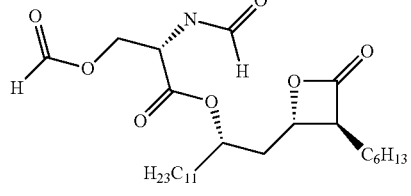 |
| 737 | 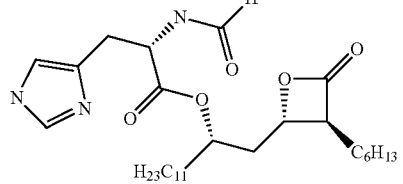 |

TABLE 1-continued

| Compound Number | Structure |
| --- | --- |
| 741 | 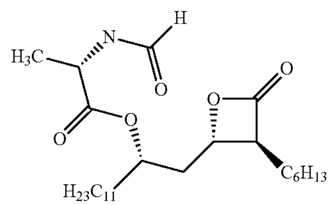 |
| 739 | 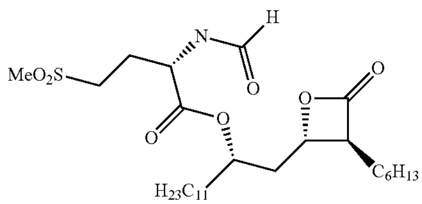 |
| 740 | 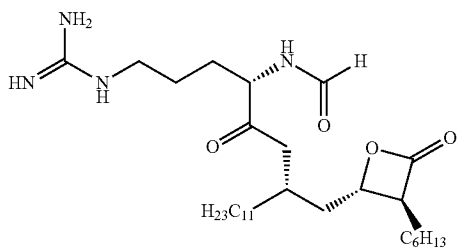 |
| 743 | 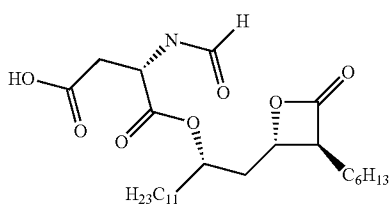 |
| 742 | 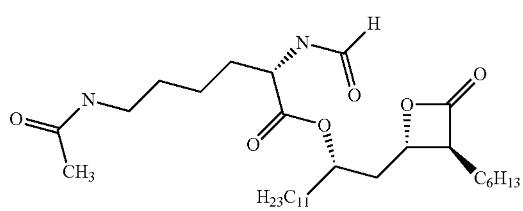 |
| 762 | 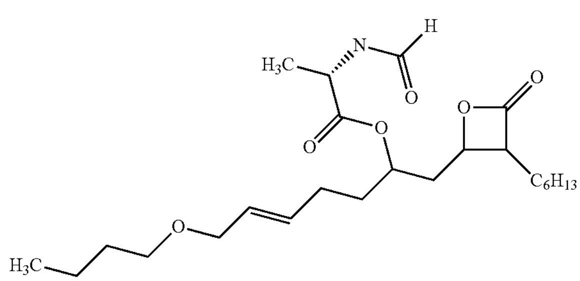 |

TABLE 1-continued

| Compound Number | Structure |
|---|---|
| 763 | (structure) |
| 760 | (structure) |
| 767 | (structure) |
| 768 | (structure) | or a pharmaceutically acceptable salt thereof. In some embodiments, the compound is

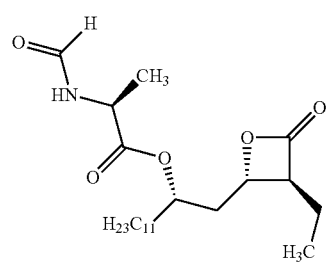

or a pharmaceutically acceptable salt thereof. In some embodiments, the compound is

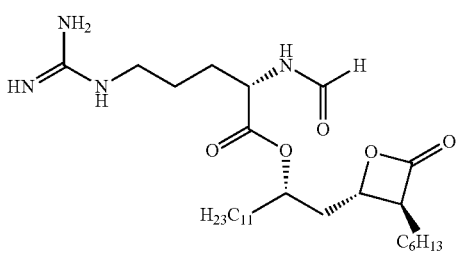

or a pharmaceutically acceptable salt thereof.

In some embodiments, a compound provided herein is stable in aqueous solution. For example, a compound provided herein can be more stable than orlistat in aqueous solution. In some embodiments, the compound is

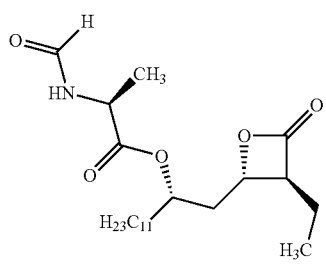

or a pharmaceutically acceptable salt thereof. In some embodiments, the compound is

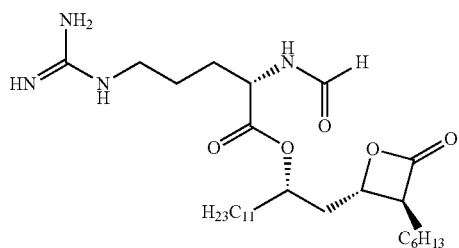

or a pharmaceutically acceptable salt thereof.

Synthesis

The compounds described herein can be prepared, for example, according to the procedures described in the Examples and associated figures.

It will be appreciated by one skilled in the art that the processes described are not the exclusive means by which compounds provided herein may be synthesized and that a broad repertoire of synthetic organic reactions is available to be potentially employed in synthesizing compounds provided herein. The person skilled in the art knows how to select and implement appropriate synthetic routes. Suitable synthetic methods of starting materials, intermediates and products may be identified by reference to the literature, including reference sources such as: *Advances in Heterocyclic Chemistry*, Vols. 1-107 (Elsevier, 1963-2012); *Journal of Heterocyclic Chemistry* Vols. 1-49 (*Journal of Heterocyclic Chemistry*, 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, 2$^{nd}$ Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry*: Reactions, *Mechanisms, and Structure*, 6$^{th}$ Ed. (Wiley, 2007); Trost et al. (Ed.), *Comprehensive Organic Synthesis* (Pergamon Press, 1991).

The reactions for preparing compounds described herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, (e.g., temperatures which can range from the solvent's freezing temperature to the solvent's boiling temperature). A given reaction can be carried out in one solvent or a mixture of more than one solvent. Depending on the particular reaction step, suitable solvents for a particular reaction step can be selected by the skilled artisan.

Preparation of compounds described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3$^{rd}$ Ed., Wiley & Sons, Inc., New York (1999).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) and normal phase silica chromatography.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

In some embodiments, the compounds described herein can contain one or more asymmetric centers and thus occur as racemates and racemic mixtures, enantiomerically enriched mixtures, single enantiomers, individual diastereomers and diastereomeric mixtures (e.g., including (R)- and (S)-enantiomers, diastereomers, (D)-isomers, (L)-isomers, (+) (dextrorotatory) forms, (−) (levorotatory) forms, the racemic mixtures thereof, and other mixtures thereof). Additional asymmetric carbon atoms can be present in a substituent, such as an alkyl group. All such isomeric forms, as well as mixtures thereof, of these compounds are expressly included in the present description. The compounds described herein can also or further contain linkages wherein bond rotation is restricted about that particular linkage, e.g. restriction resulting from the presence of a ring or double bond (e.g., carbon-carbon bonds, carbon-nitrogen bonds such as amide bonds). Accordingly, all cis/trans and E/Z isomers and rotational isomers are expressly included in the present description. Unless otherwise mentioned or indicated, the chemical designation of a compound encompasses the mixture of all possible stereochemically isomeric forms of that compound.

Optical isomers can be obtained in pure form by standard procedures known to those skilled in the art, and include, but are not limited to, diastereomeric salt formation, kinetic resolution, and asymmetric synthesis. See, for example, Jacques, et al., Enantiomers, Racemates and Resolutions (Wiley Interscience, New York, 1981); Wilen, S. H., et al., Tetrahedron 33:2725 (1977); Eliel, E. L. Stereochemistry of Carbon Compounds (McGraw-Hill, NY, 1962); Wilen, S. H. Tables of Resolving Agents and Optical Resolutions p. 268 (E. L. Eliel, Ed., Univ. of Notre Dame Press, Notre Dame, Ind. 1972), each of which is incorporated herein by reference in their entireties. It is also understood that the compounds described herein include all possible regioisomers, and mixtures thereof, which can be obtained in pure form by standard separation procedures known to those skilled in the art, and include, but are not limited to, column chromatography, thin-layer chromatography, and high-performance liquid chromatography.

Unless specifically defined, compounds provided herein can also include all isotopes of atoms occurring in the intermediates or final compounds. Isotopes include those atoms having the same atomic number but different mass numbers. Unless otherwise stated, when an atom is designated as an isotope or radioisotope (e.g., deuterium, [$^{11}$C], [$^{18}$F]), the atom is understood to comprise the isotope or radioisotope in an amount at least greater than the natural abundance of the isotope or radioisotope. For example, when an atom is designated as "D" or "deuterium", the position is understood to have deuterium at an abundance that is at least 3000 times greater than the natural abundance of deuterium, which is 0.015% (i.e., at least 45% incorporation of deuterium).

All compounds, and pharmaceutically acceptable salts thereof, can be found together with other substances such as water and solvents (e.g. hydrates and solvates) or can be isolated.

In some embodiments, preparation of compounds can involve the addition of acids or bases to affect, for example, catalysis of a desired reaction or formation of salt forms such as acid addition salts.

Example acids can be inorganic or organic acids and include, but are not limited to, strong and weak acids. Some example acids include hydrochloric acid, hydrobromic acid, sulfuric acid, phosphoric acid, p-toluenesulfonic acid, 4-nitrobenzoic acid, methanesulfonic acid, benzenesulfonic acid, trifluoroacetic acid, and nitric acid. Some weak acids include, but are not limited to acetic acid, propionic acid, butanoic acid, benzoic acid, tartaric acid, pentanoic acid, hexanoic acid, heptanoic acid, octanoic acid, nonanoic acid, and decanoic acid.

Example bases include lithium hydroxide, sodium hydroxide, potassium hydroxide, lithium carbonate, sodium carbonate, potassium carbonate, and sodium bicarbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include lithium, sodium, and potassium salts of methyl, ethyl, n-propyl, iso-propyl, n-butyl, tert-butyl, trimethylsilyl and cyclohexyl substituted amides.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present application include the conventional non-toxic salts of the parent compound formed, for example, from non-toxic inorganic or organic acids. The pharmaceutically acceptable salts of the present application can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (MeCN) are preferred. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977). Conventional methods for preparing salt forms are described, for example, in *Handbook of Pharmaceutical Salts: Properties, Selection, and Use*, Wiley-VCH, 2002.

Pharmaceutical Compositions

When employed as pharmaceuticals, the compounds provided herein and pharmaceutically acceptable salts thereof can be administered in the form of pharmaceutical compositions. These compositions can be prepared as described herein or elsewhere, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral, or parenteral. Parenteral administration includes intravenous, intraarterial, subcutaneous, intraperitoneal intramuscular or injection or infusion; or intracranial, (e.g., intrathecal or intraventricular, administration). Parenteral administration can be in the form of a single bolus dose, or may be, for example, by a continuous perfusion pump. In some embodiments, the compounds provided herein, or a pharmaceutically acceptable salt thereof, are suitable for parenteral administration. In some embodiments, the compounds provided herein are suitable for intravenous administration. In some embodiments, the compounds provided herein are suitable for oral administration. In some embodiments, the compounds provided herein are suitable for topical administration.

Pharmaceutical compositions and formulations for topical administration may include, but are not limited to, transdermal patches, ointments, lotions, creams, gels, drops, suppositories, sprays, liquids and powders. Conventional pharmaceutical carriers, aqueous, powder or oily bases, thickeners and the like may be necessary or desirable. In some embodiments, the pharmaceutical compositions provided herein are suitable for parenteral administration. In some embodiments, the compounds provided herein can be formulated for topical delivery (e.g., for the treatment of acne). An exemplary formulation includes:

about 10 to about 50 mM of a compound provided herein (e.g., a compound 767)

about 50% (v/v) 99.5-100% ethanol or isopropanol
about 0.25 to about 2% (w/v) carbomer (e.g, carbomer 934 or carbomer 940)
about 0.5 to about 1% (w/v) trolamine
water (to 100%).

In some embodiments, the pharmaceutical compositions provided herein are suitable for intravenous administration. In some embodiments, the pharmaceutical compositions provided herein are suitable for oral administration. In some embodiments, the pharmaceutical compositions provided herein are suitable for topical administration.

Also provided are pharmaceutical compositions which contain, as the active ingredient, a compound provided herein, or a pharmaceutically acceptable salt thereof, in combination with one or more pharmaceutically acceptable carriers (e.g. excipients). In making the pharmaceutical compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be, for example, in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders.

Some examples of suitable excipients include, without limitation, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include, without limitation, lubricating agents such as talc, magnesium stearate, and mineral oil; wetting agents; emulsifying and suspending agents; preserving agents such as methyl- and propylhydroxy-benzoates; sweetening agents; flavoring agents, or combinations thereof.

The active compound can be effective over a wide dosage range and is generally administered in an effective amount. It will be understood, however, that the amount of the compound actually administered will usually be determined by a physician, according to the relevant circumstances, including the condition to be treated, the chosen route of administration, the actual compound administered, the age, weight, and response of the individual subject, the severity of the subject's symptoms, and the like.

The compositions provided herein can be administered one from one or more times per day to one or more times per week; including once every other day. The skilled artisan will appreciate that certain factors can influence the dosage and timing required to effectively treat a subject, including, but not limited to, the severity of the disease or disorder, previous treatments, the general health and/or age of the subject, and other diseases present. Moreover, treatment of a subject with a therapeutically effective amount of a compound described herein can include a single treatment or a series of treatments. In some embodiments, the compositions provided herein are administered as a single dose.

Dosage, toxicity and therapeutic efficacy of the compounds provided herein can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds exhibiting high therapeutic indices are preferred. While compounds that exhibit toxic side effects can be used, care should be taken to design a delivery system that targets such compounds to the site of affected tissue in order to minimize potential damage to uninfected cells and, thereby, reduce side effects. In some embodiments, the compounds provided herein exhibit lower toxicity as compared to similar dosages of orlistat. Evaluation of toxicity may be determined, for example, using methods such as those described herein.

Methods of Treatment

The present disclosure further provides methods for the treatment of disorders associated with elevated lipid concentrations (e.g., lipotoxicity). A number of such disorders are known in the art and can be readily identified by one of skill in the art. In some embodiments, the methods include a method for inhibiting serum lipases in a subject in need thereof, the method comprising administering to the subject a therapeutically effective amount of a compound provided herein, or a pharmaceutically acceptable salt thereof. In some embodiments, the compounds provided herein decrease serum lipase concentrations. In some embodiments, the lipase is a pancreatic lipase such as human pancreatic tri-acyl glycerol lipase (hPNLIP), human pancreatic lipase related protein 2 (hPLRP2) and human colipase (hCEL). In some embodiments, the compounds provided herein can reduce or inhibit generation of free fatty acids. For example, the compounds provided herein can decrease serum concentrations of free fatty acids.

As used herein, the term "subject," refers to any animal, including mammals. For example, the term "subject" includes, but is not limited to, mice, rats, other rodents, rabbits, dogs, cats, swine, cattle, sheep, horses, primates, and humans. In some embodiments, the subject is a human. In some embodiments, the subject is obese. The term "obese" as used herein refers to a subject having a body mass index of greater than 23, 25 and particularly greater than or equal to 30. Alternatively it could an increase in abdominal fat or girth more than normal for the race, ethnicity, sex or nationality of the individual.

In some embodiments, the methods described herein can include in vitro methods, e.g., contacting a sample (e.g., a cell or tissue) with a compound provided herein, or a pharmaceutically acceptable salt thereof.

In some embodiments, the disorder is acute pancreatitis. For example, the acute pancreatitis can be severe. In some embodiments, the methods provided herein can be useful in downgrading a severe case of acute pancreatitis to a mild case of pancreatitis. The disclosure provides methods of treating one or more symptoms of pancreatitis in a subject in need thereof by administering a therapeutically effective amount of a compound provided herein, or a pharmaceutically acceptable salt thereof, to treat one or more symptoms of acute pancreatitis. Exemplary symptoms of acute pancreatitis include abdominal pain, back pain, swollen abdomen, nausea, vomiting, fever, rapid pulse, shortness of breath, low body temperature and the like.

Non-limiting embodiments of the invention provide for a method of reducing the risk of organ failure in a subject suffering from acute pancreatitis comprising administering, to the subject, an effective amount of a pancreatic lipase inhibitor. Organs for which the risk of organ failure may be reduced include the kidney (where failure is referred to as renal failure), the lung (where failure is referred to as pulmonary failure), Shock with low blood pressure or an increase in heart rate or the appearance of pulmonary edema (noted as crackles on auscultation, or CXR, or CT scan) as well as multisystem organ failure (e.g. multiple organ dysfunction syndrome involving at least these two organs). The status of these organs may be determined using clinical methods well known in the art. For example, and not by way of limitation, kidney function (and the development of renal failure) may be assessed via increased blood urea nitrogen levels, increased creatinine, decreased urine output, and/or histologic findings; lung function and the development of pulmonary failure may be assessed using pulmonary function tests, blood gases (oxygen and carbon dioxide levels), oxygen supplementation requirements (e.g. nasal cannula or face mask or ventilator, with different percentages and flow rates of oxygen) and/or histologic findings; (for indices of organ failure, see J. Wallach, 1978, Interpretation of Diagnostic Tests, Third Edition, Little, Brown and Co., Boston, and/or J. Wallach, 2006, Interpretation of Diagnostic Tests, Eighth Edition, Lippincott Williams & Wilkins, both incorporated by reference in their entireties). Likewise, an index of systemic inflammation is an increase in levels of one or more inflammatory mediators, including but not limited to CRP, or parts of systemic inflammatory response syndrome (SIRS) criteria, tumor necrosis factor alpha, monocyte chemotactic protein 1 and/or interleukin 6. These embodiments are supported, at least in part, by working examples below, which show the effectiveness of pancreatic lipase inhibitors in decreasing the risk of multisystem organ failure.

In some embodiments, the compounds provided herein are useful for reducing the risk of secondary effects of acute pancreatitis in a subject in need thereof. For example, the risk of developing shock can be reduced. In some embodiments, the risk of developing renal failure is reduced. In some embodiments, the risk of developing pulmonary failure is reduced.

In some embodiments, the disorder is acne. In other embodiments, the disorder is trauma, hemorrhage, critical illness, or sepsis. For example, the sepsis is culture negative sepsis. In some embodiments, the disorder is a burn. In other embodiments, the disorder is an infection. For example, the infection may be caused by one or more organisms selected from the group consisting of *P. auregenosa, S. aureus, B. subtilis,* and *B. cepecia.* See, for example, Ryan C M, Sheridan R L, Schoenfeld D A, Warshaw A L, Tompkins R G: *Postburn pancreatitis. Ann Surg* 1995, 222(2):163-170; Subramanian A, Albert V, Mishra B, Sanoria S, Pandey R M: *Association Between the Pancreatic Enzyme Level and Organ Failure in Trauma Patients. Trauma Mon* 2016, 21(2):e20773; Malinoski D J, Hadjizacharia P, Salim A, Kim H, Dolich M O, Cinat M, Barrios C, Lekawa M E, Hoyt D B: *Elevated serum pancreatic enzyme levels after hemorrhagic shock predict organ failure and death. J Trauma* 2009, 67(3):445-449; Lee C C, Chung W Y, Shih Y H: *Elevated amylase and lipase levels in the neurosurgery intensive care unit. J Chin Med Assoc* 2010, 73(1):8-14; and Manjuck J, Zein J, Carpati C, Astiz M: *Clinical significance of increased lipase levels on admission to the ICU. Chest* 2005, 127(1):246-250.

EXAMPLES

Example 1. Preparation and Testing of Non-Formylated Amino Acid Analogs

Figure 3:
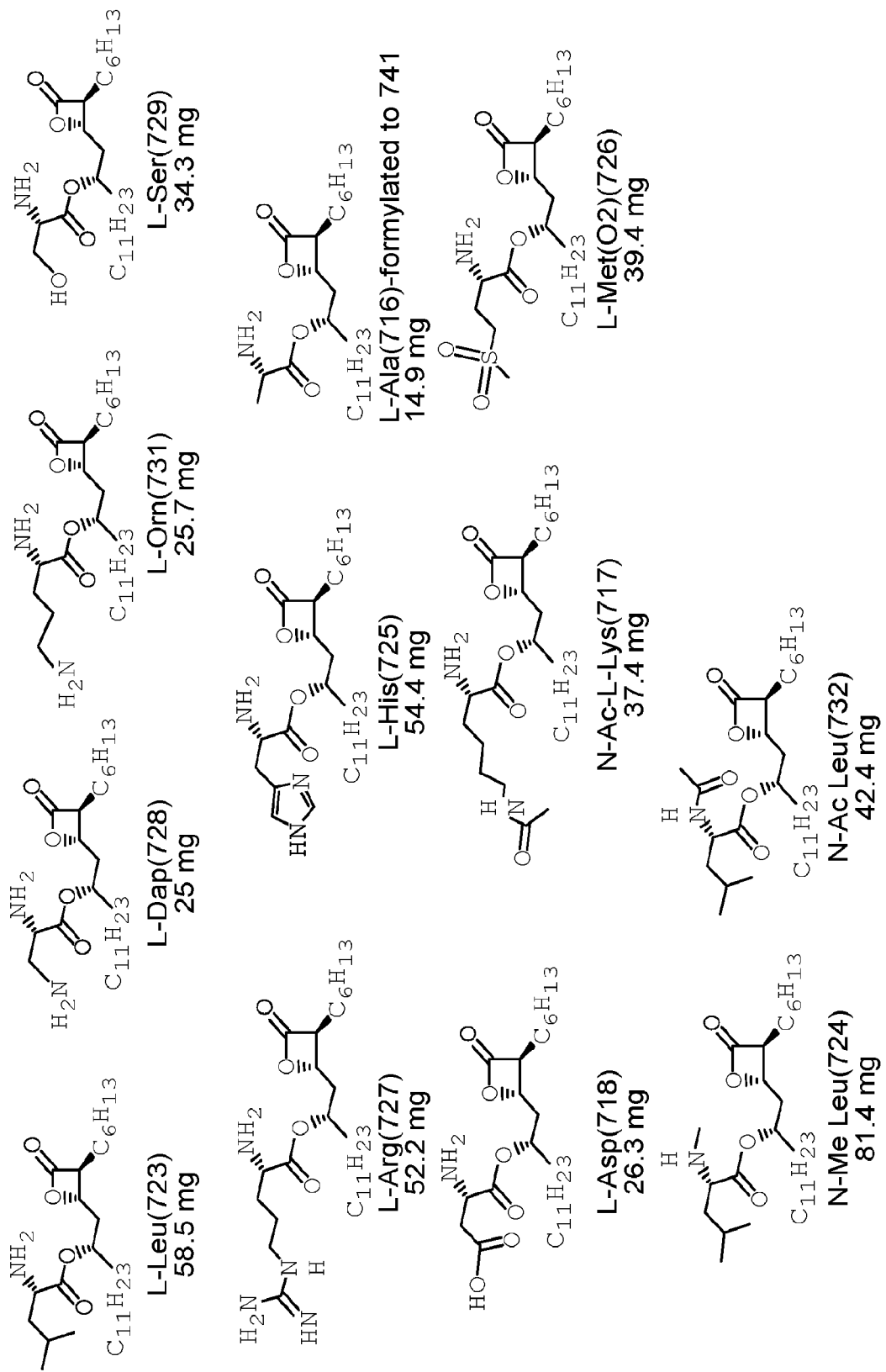
FIG. 3 shows the structures of the various non-formylated amino ester modified analog compounds prepared.

A number of non-formylated amino acid analogs were prepared in which the L-amino-ester leucine was replaced by alternates. The synthetic steps involved in this process are outlined in FIG. 2. As shown in FIG. 3, the compounds generated included compounds where the L-leucine (#723, which is also orlistat) amino-ester was replaced by alternates such as N-methyl leucine (#724) or more polar or shorter alternates, including L-alanine (#716), N-acetyl-L-cystine (#717), L-aspartate (#718), L-histidine (#725), L-methionine sulfone (#726), L-arginine (727), L-diaminopimelic acid (#728), L-serine (#729), L-ornithine (#731), or N-acetyl leucine (#732).

Figure 4A:
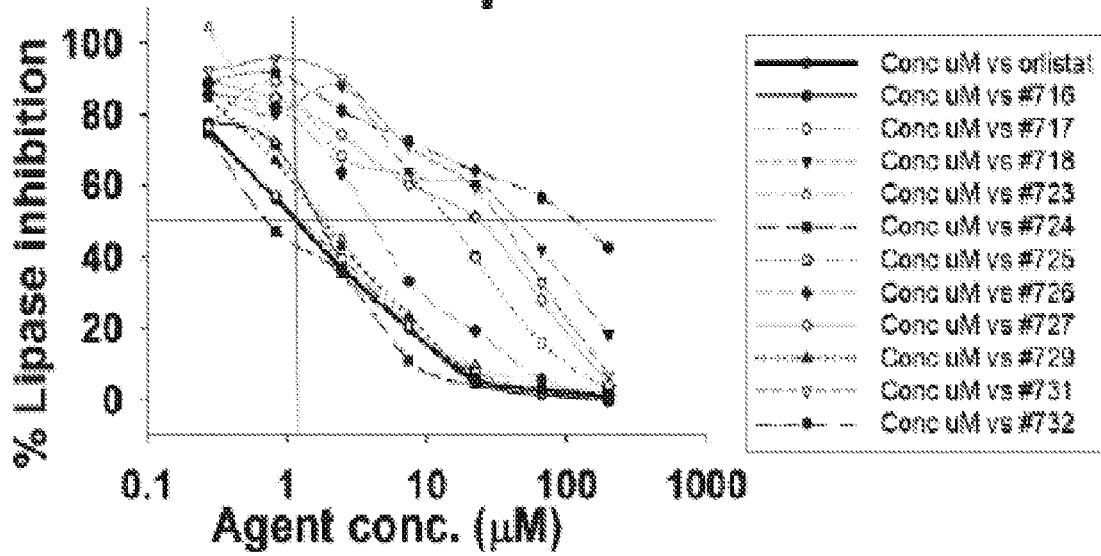
FIG. 4A provides the results of freshly prepared solutions of the compounds while FIG. 4B provides the results of solutions stored overnight.
Figure 4B:
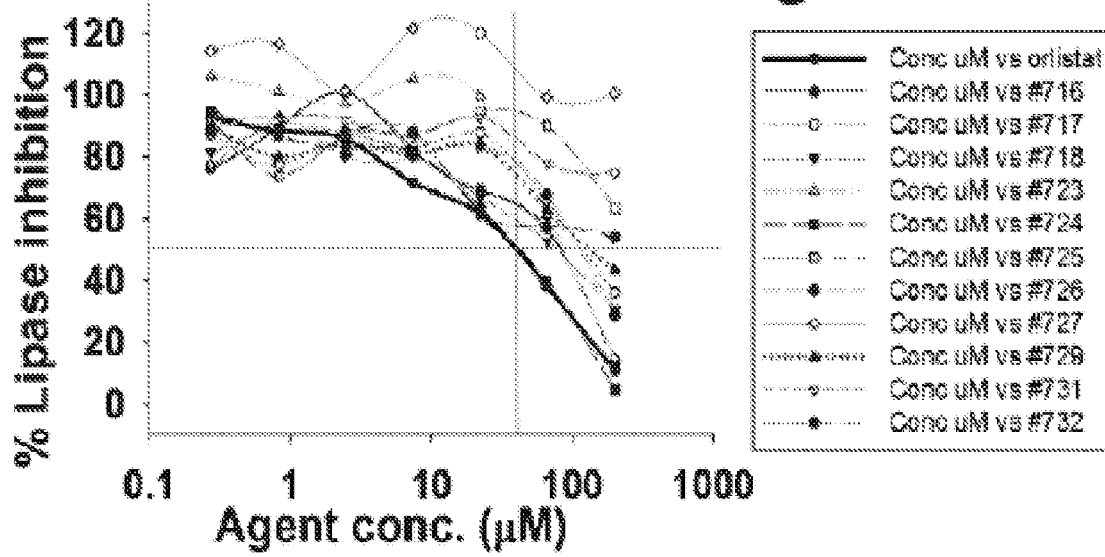
FIG. 4 provides line graphs showing the results of a lipase inhibition assay testing the non-formylated amino ester modified analog compounds.

To test the efficacy of these compounds, the agents were dissolved as a 20 mM stock in ethanol, and further diluted to in PBS as a 600 micromolar working stock (3.3% ethanol). This was either used immediately or left at room temperature for 16-20 hours overnight before retesting efficacy. The agents were incubated with a pancreatic lysate in serial ⅓ dilutions spanning a range of 200 to 0.3 micromolars for 30 minutes. 5 microliters of these mixtures were then used to measure lipase activity using a commercial lipase assay (Pointe scientific) containing a monoacyl glycerol lipase in the reagent. The lipase assay was done using reagents in proportion to the recommended protocol. Values were depicted as % maximal lipase activity of the well without any inhibitor. As can be seen there was no increase in efficacy of the non-formylated orlistat analogs over that of orlistat (FIG. 4).

Example 2. Preparation and Testing of Formylated Amino Acid Analogs

Figure 5:
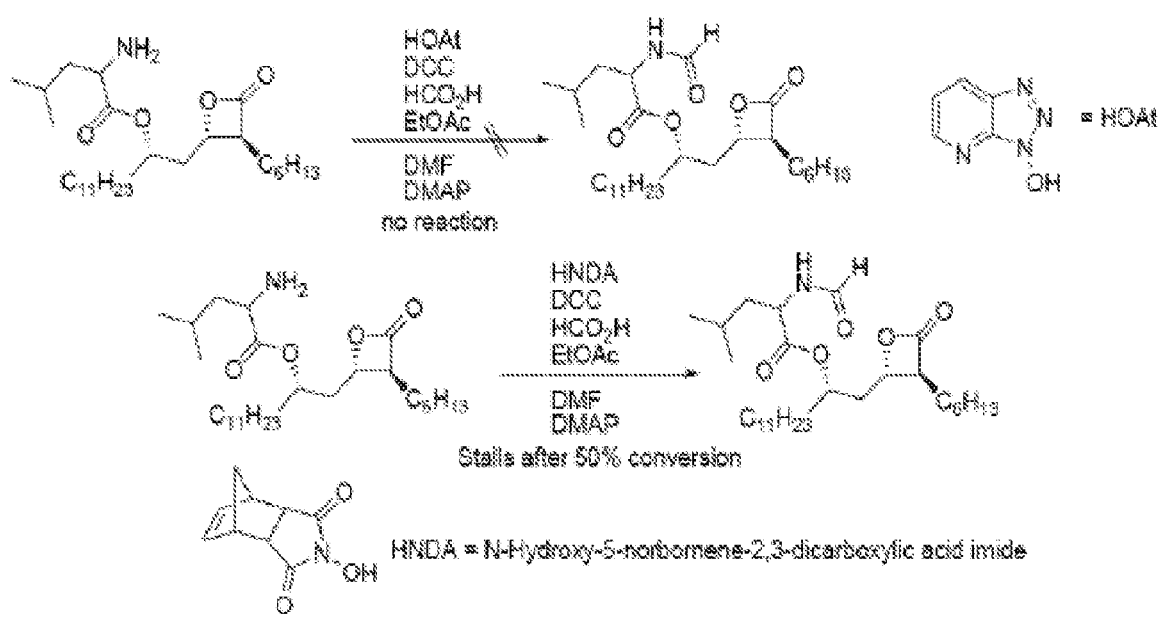
FIG. 5 is a scheme detailing a synthetic route to prepare formulated amino ester modified analogs.

A number of formylated amino acid analogs were prepared in which the L-amino-ester leucine was replaced by alternates. The synthetic steps involved in this process are outlined in FIG. 2 and FIG. 5.

Figure 6:
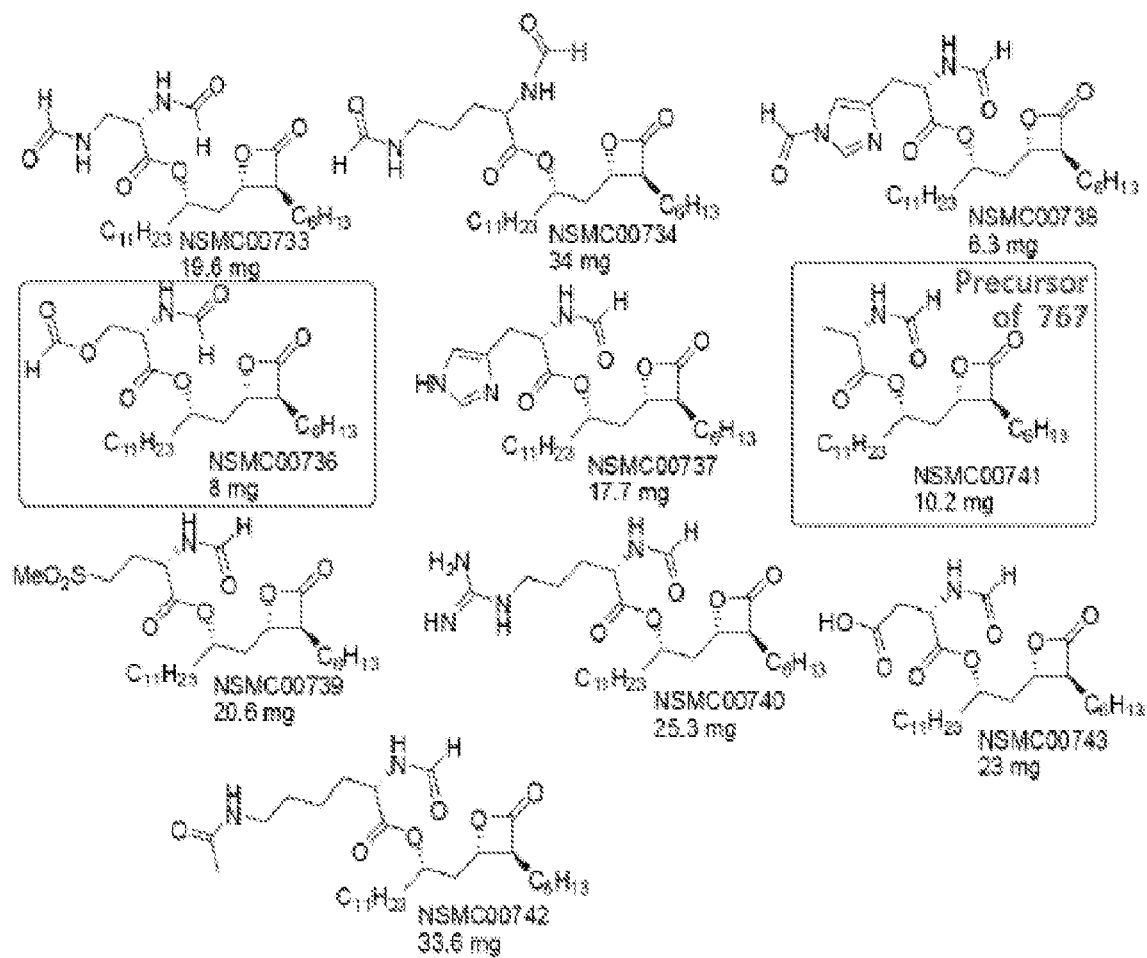
FIG. 6 shows the structures of the various formyl amino ester modified analog compounds prepared.
Figure 7A:
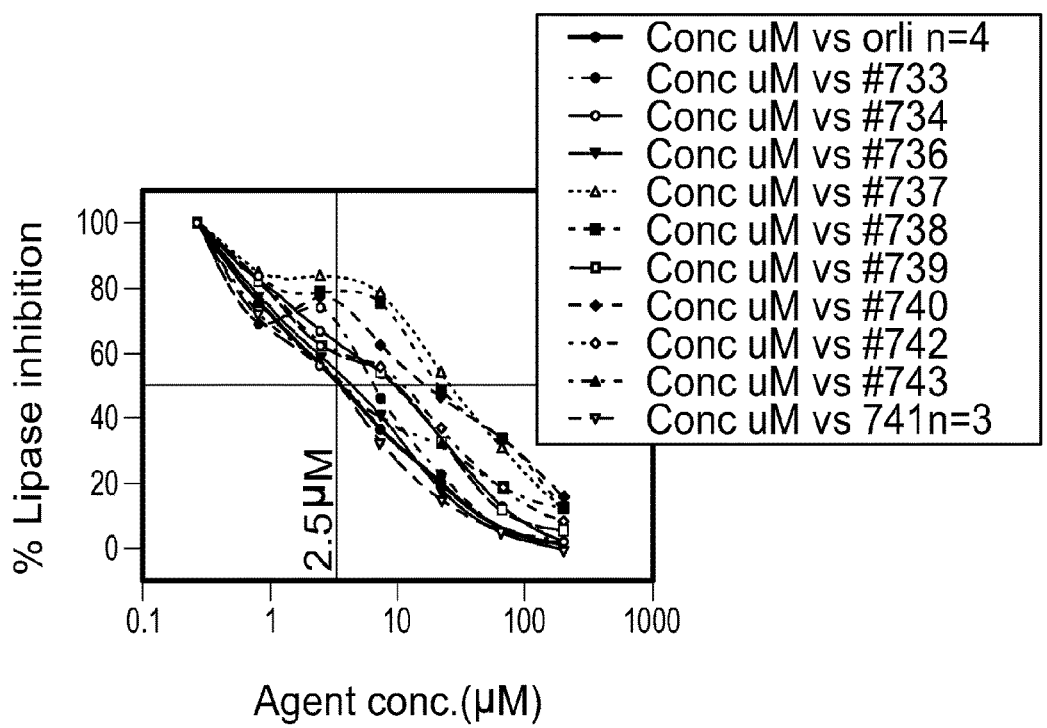
FIG. 7A provides the results of freshly prepared solutions of the compounds while FIG. 7B provides the results of solutions stored overnight.
Figure 7B:
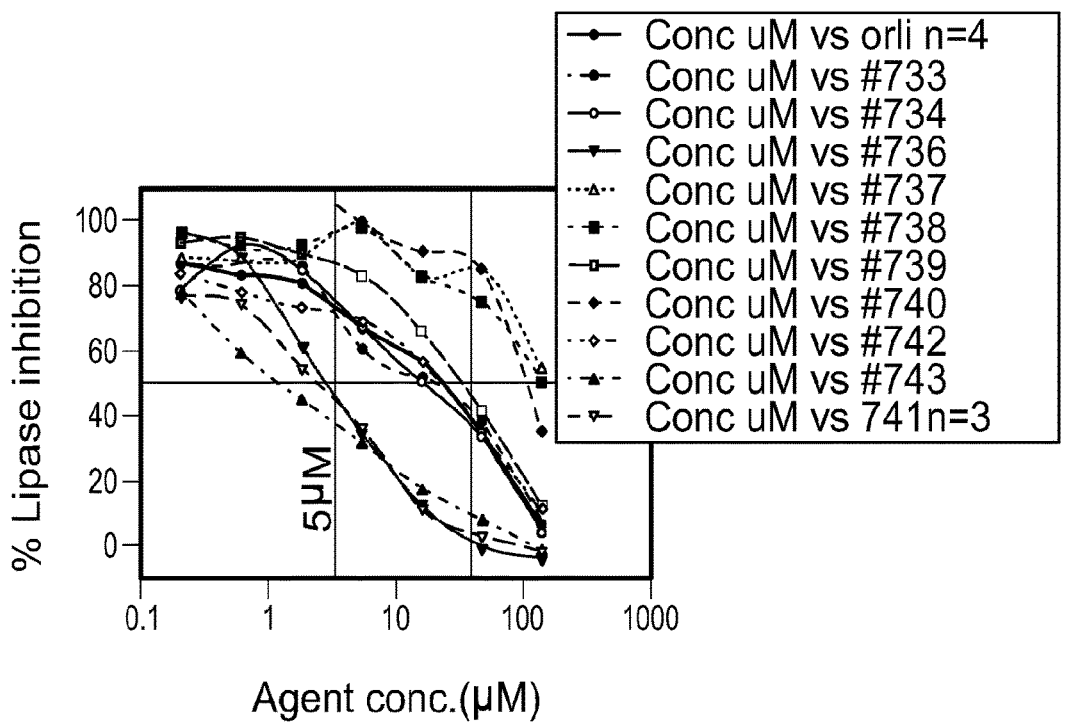
FIG. 7 provides line graphs showing the results of a lipase inhibition assay testing the formyl amino ester modified analog compounds.
Figure 8A:
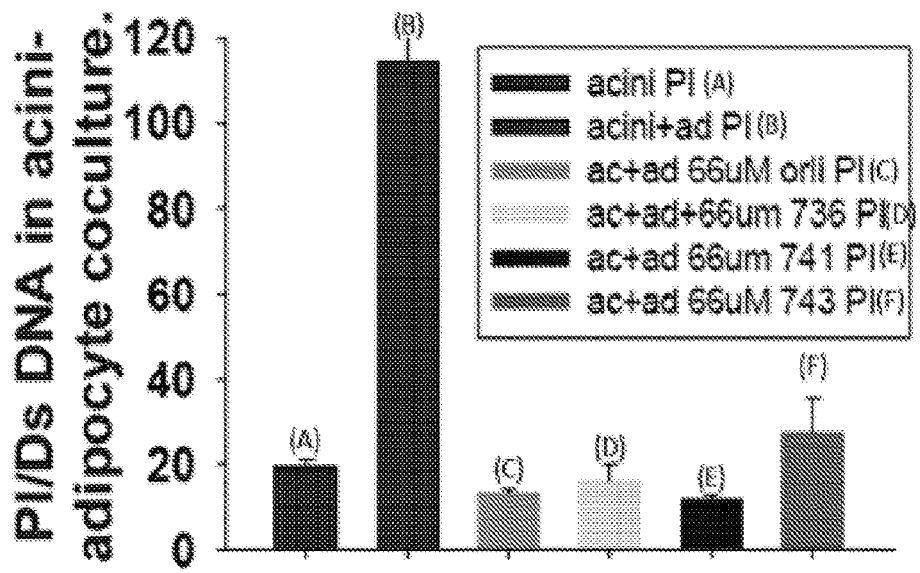
FIG. 8 provides bar graphs detailing the efficacy of selected analog compounds in reducing lipotoxic damage to acinar cells in acinar-adipocyce co-culture (FIG. 8A) while also assessing the toxicity of the compounds to these cells (FIG. 8B).
Figure 8B:
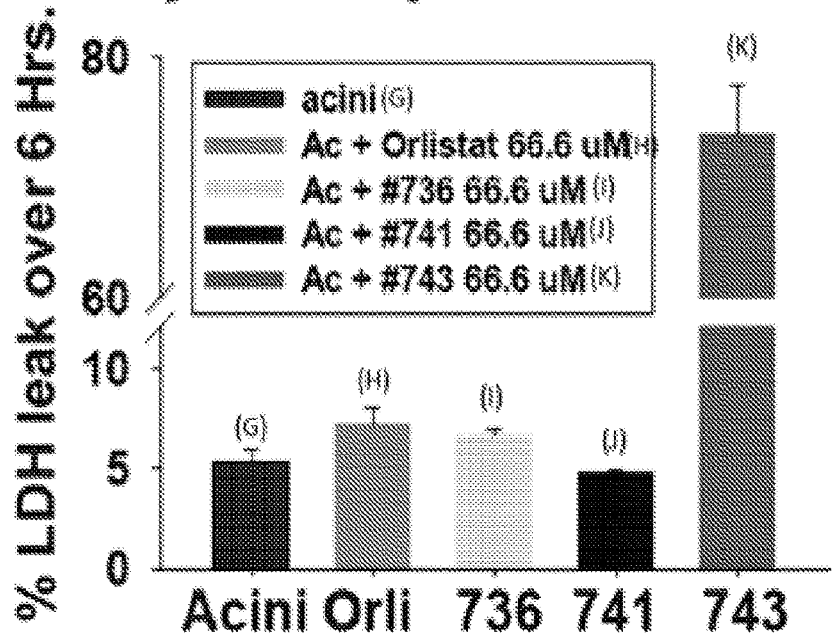
Figure 9:
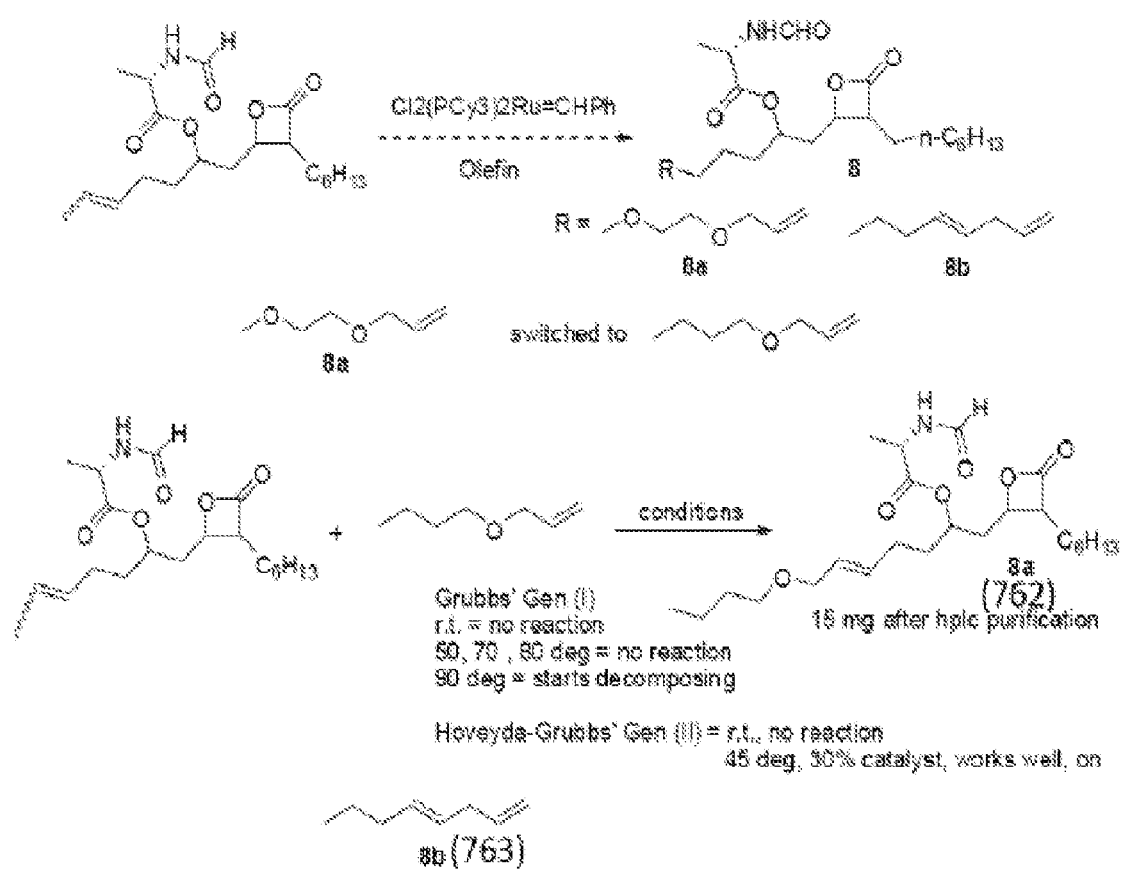
FIG. 9 is a scheme detailing the metastasis reaction used to prepare the β-chain analogs.
Figure 10:
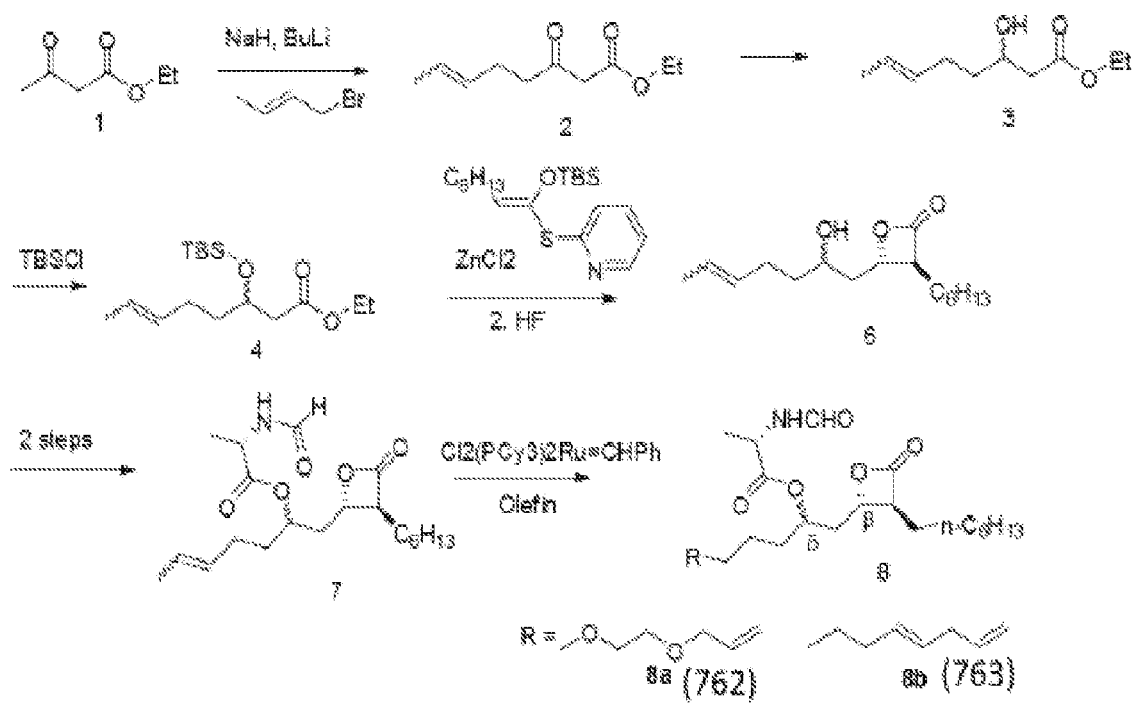
FIG. 10 is a scheme detailing a synthetic route to the β-chain analogs.
Figure 11:
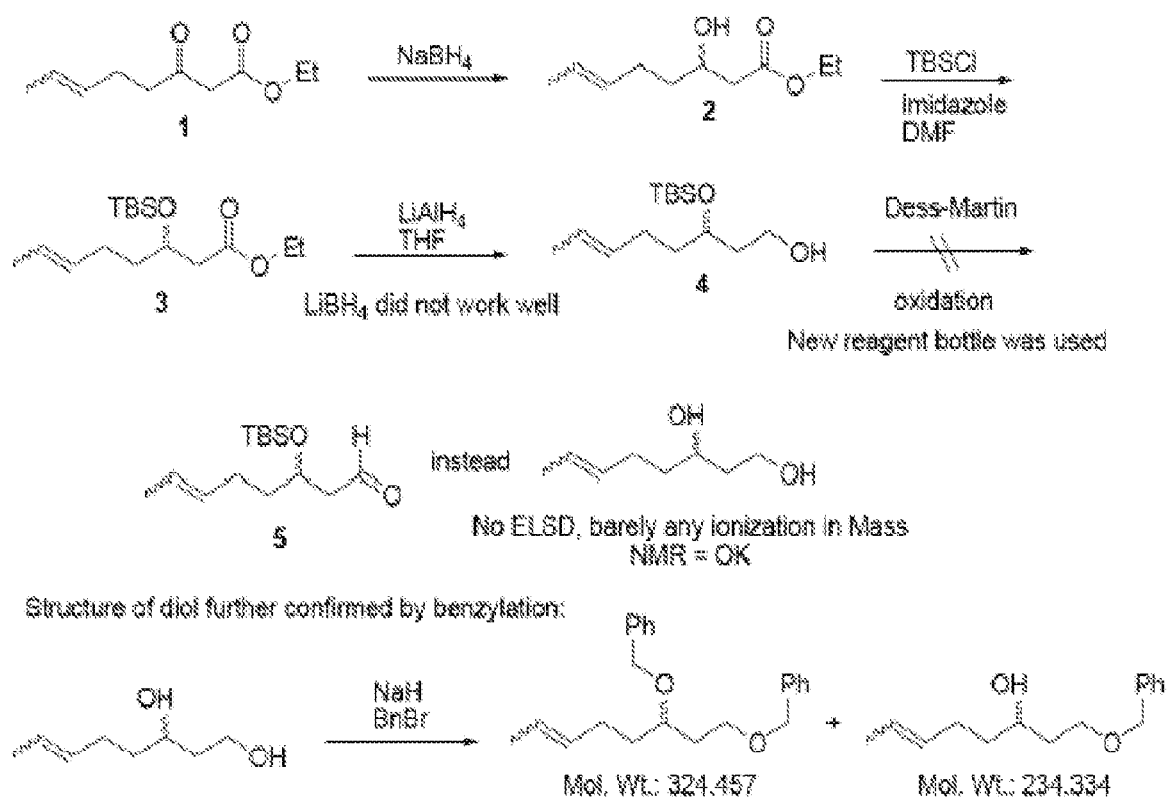
FIG. 11 is a scheme detailing a synthetic route to the β-chain analogs.
Figure 12:
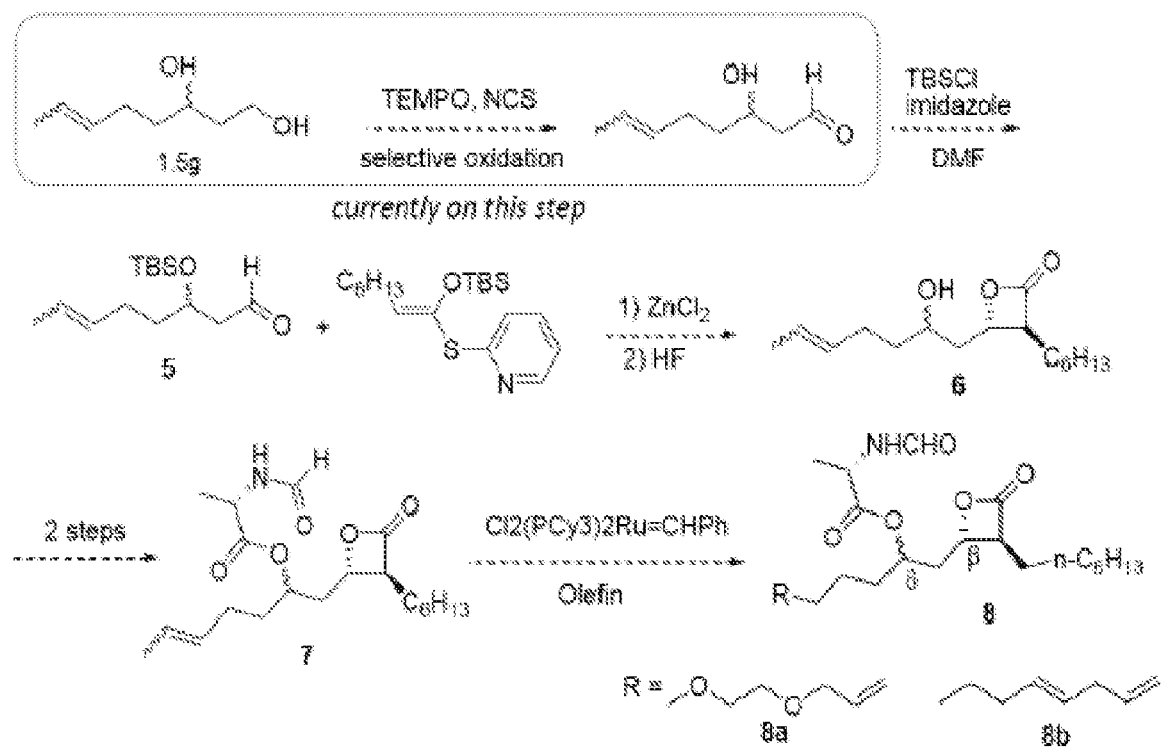
FIG. 12 is a scheme detailing a synthetic route to the β-chain analogs.
Figure 13:
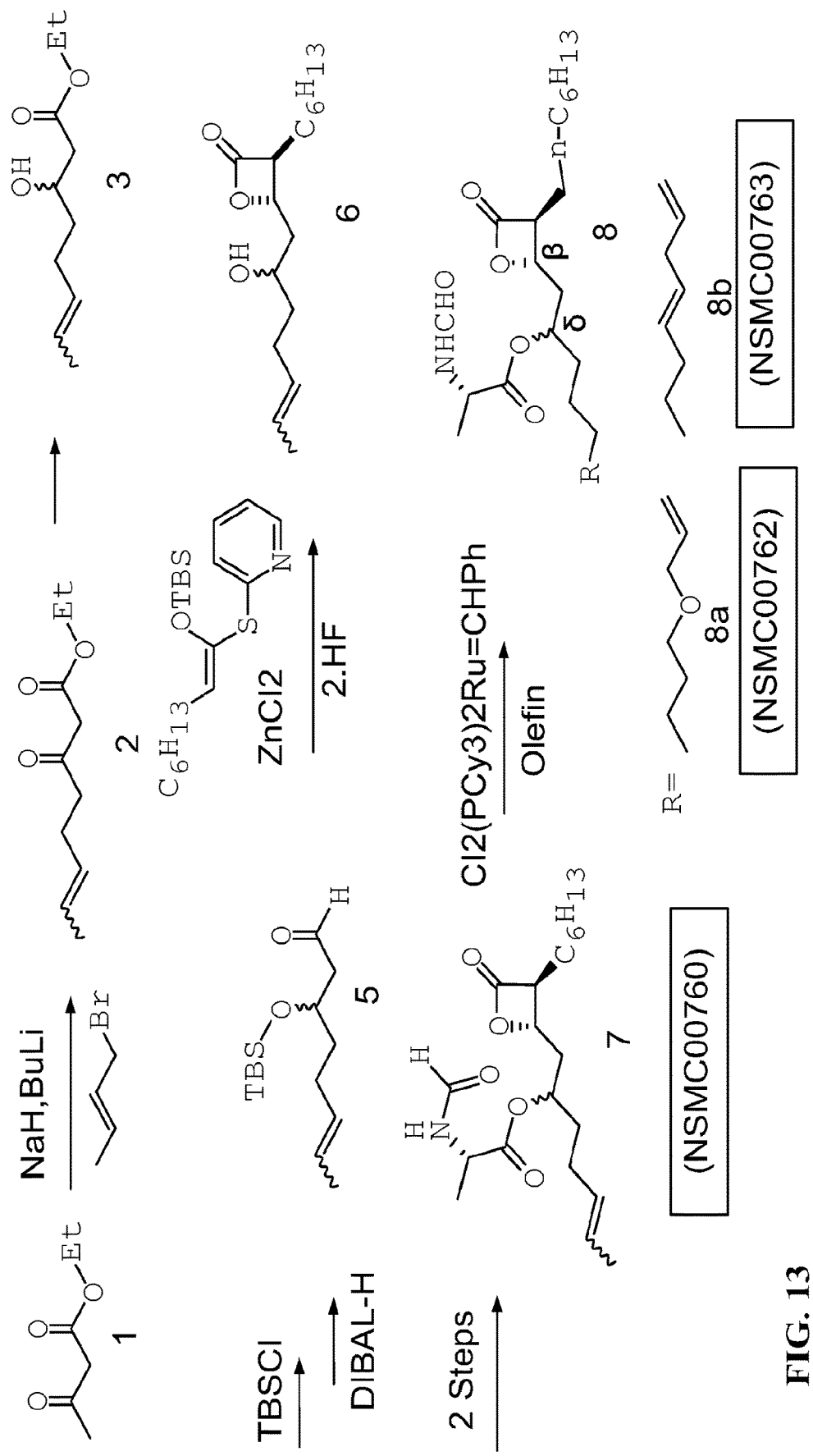
FIG. 13 is a scheme detailing a synthetic route to the β-chain analogs.
Figure 14:
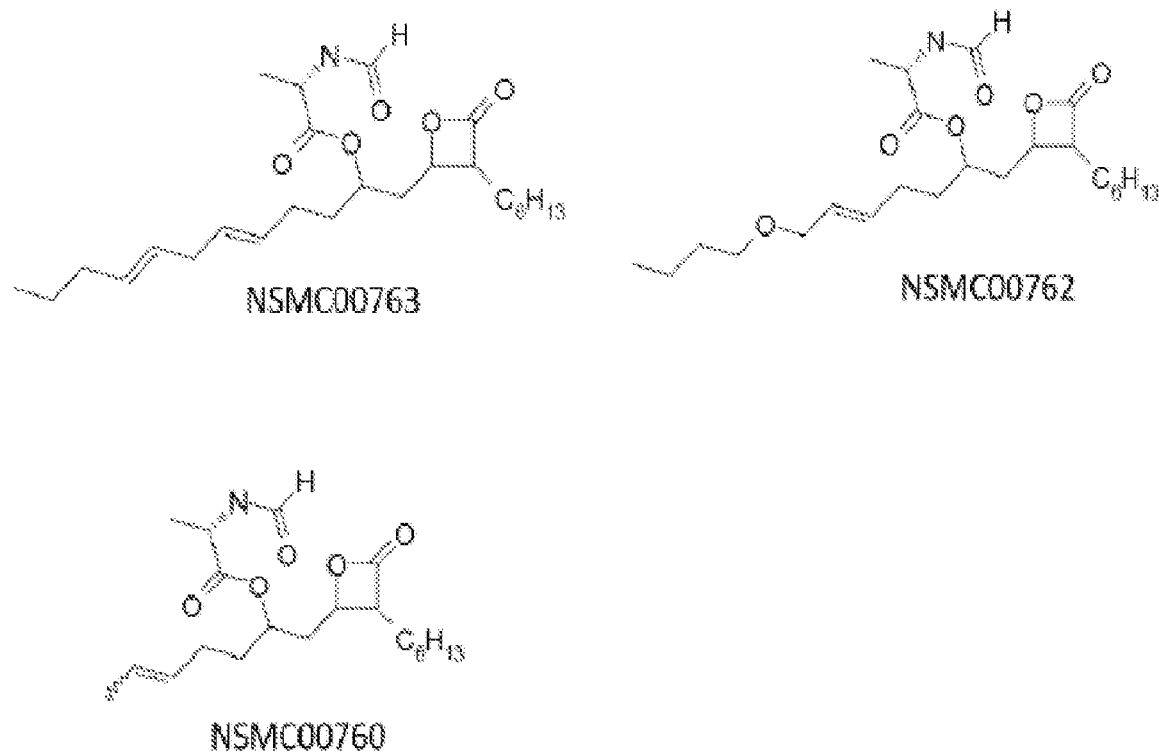
FIG. 14 shows the structures of the various β-chain analogs prepared.

These agents (#733, 734, 738, 739, 740, 742, 743, as shown in FIG. 6) were initially tested as described in Example 1. It was noted that compounds 741, 736, 743 had an approximately 10-fold improvement in stability and efficacy over orlistat after overnight storage (FIG. 7). The compounds were further tested for efficacy in reducing lipotoxic damage to acinar cells in acinar-adipocyte co-culture as described in Navina S, Acharya C, DeLany J P, Orlichenko L S, Baty C J, Shiva S S, Durgampudi C, Karlsson J M, Lee K, Bae K T et al: *Lipotoxicity causes multisystem organ failure and exacerbates acute pancreatitis in obesity. Sci Transl Med* 2011, 3(107):107ra110 (FIG. 8A), and while all agents were effective at 66 micromolars (the nearest concentration to $IC_{50}$ of orlistat after overnight incubation), compound 743 was noted to be toxic to acinar cells (FIG. 8B) and compound 741 was the least toxic at this concentration, while retaining its efficacy. Compound 736 also retained its efficacy at low toxicities.

Example 3. Preparation and Testing of β-Chain Analogs

Figure 15:
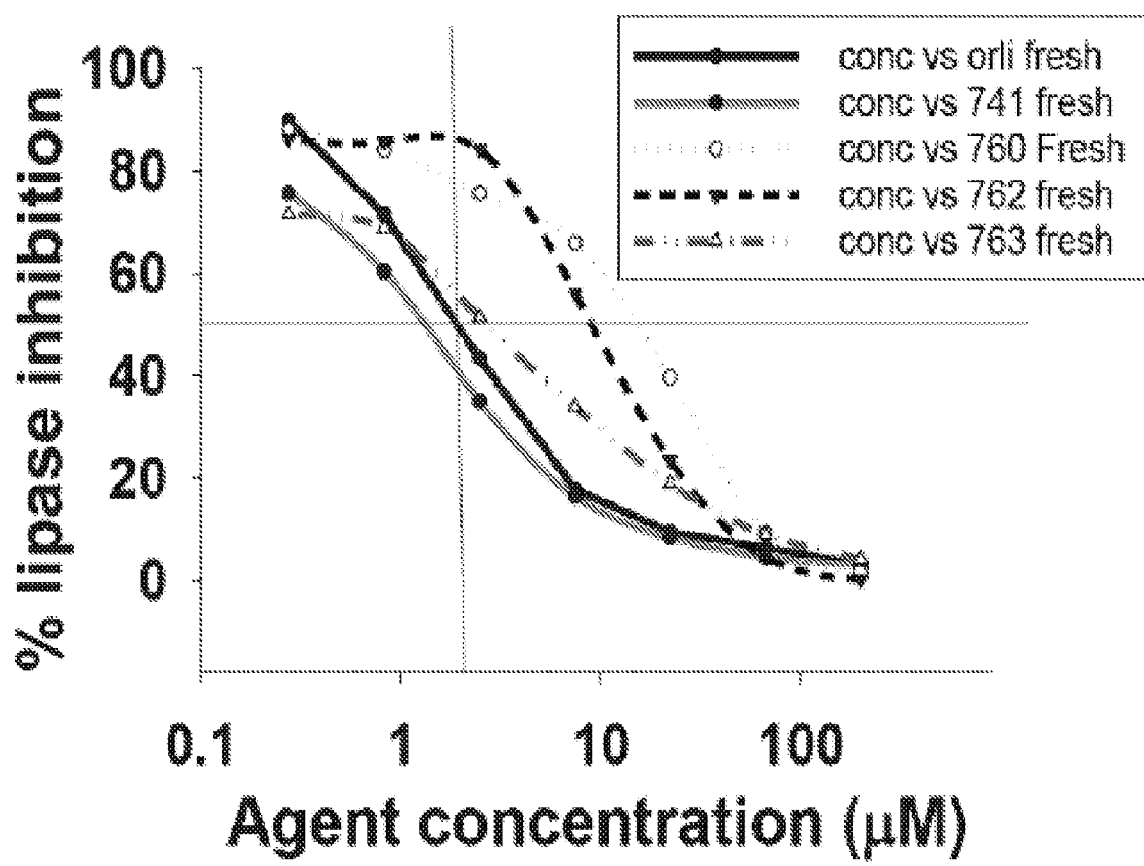
FIG. 15 provides a line graph showing the results of a lipase inhibition assay testing the β-chain analogs in freshly prepared solutions.

To further explore options for improving efficacy of the analogs, the beta chain of 741 was altered to make it more hydrophilic. For this, compounds 760, 762, 763 were prepared as described in FIGS. 9-14. The modifications at this position were associated with no improvement in the lipase inhibition efficacy, and, in fact, a decrease in efficacy was observed. See FIG. 15.

Example 4. Preparation and Testing of α-Chain Analogs

Figure 16:
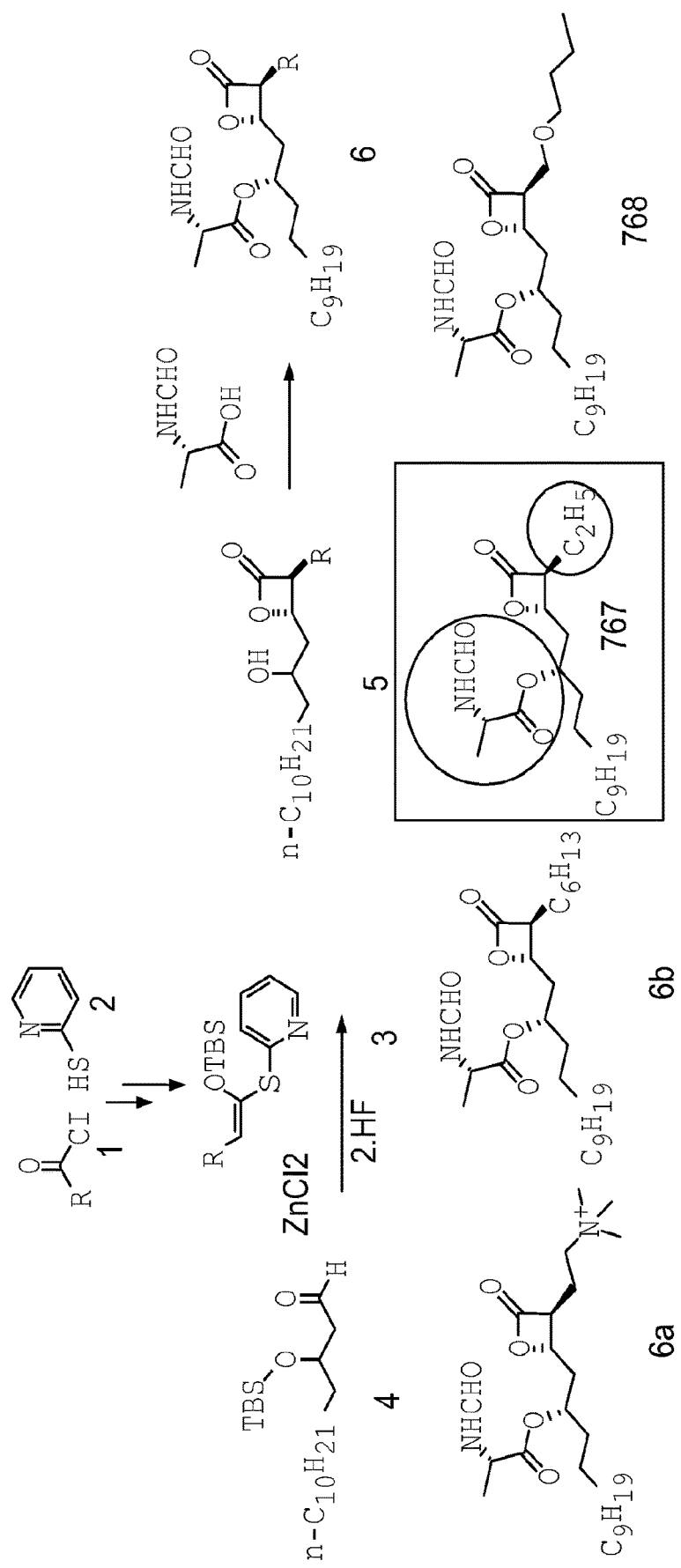
FIG. 16 is a scheme detailing a synthetic route to the α-chain analogs.
Figure 17A:
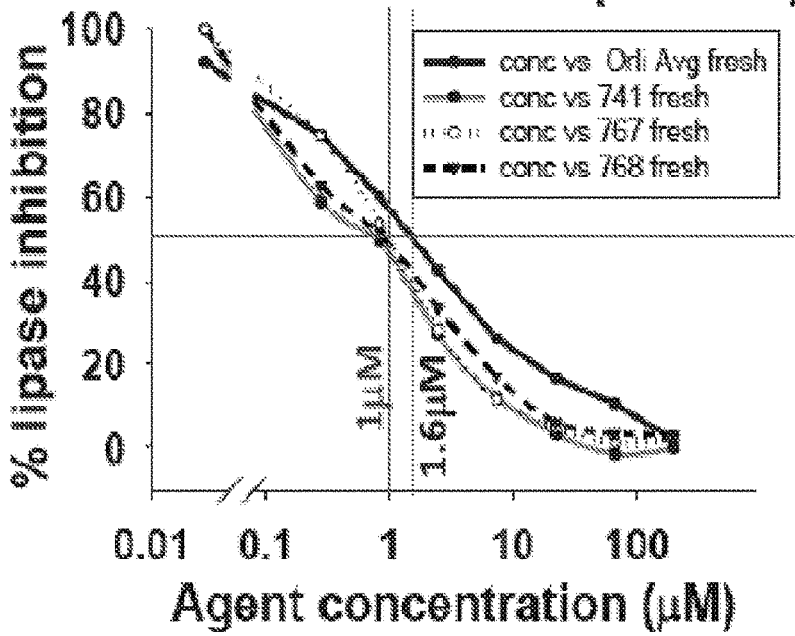
FIG. 17A provides the results of freshly prepared solutions of the compounds while FIG. 17B provides the results of solutions stored overnight.
Figure 17B:
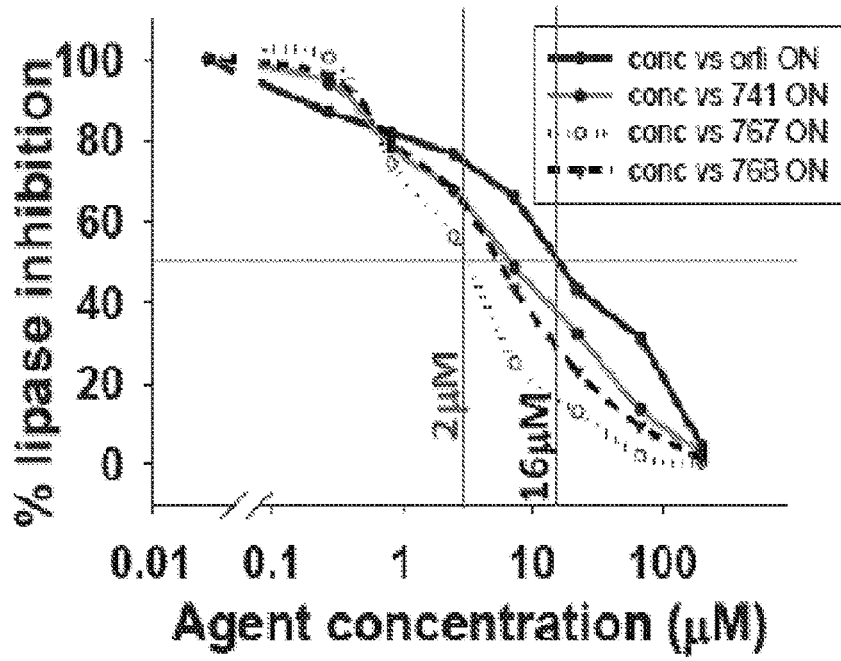
FIG. 17 provides line graphs showing the results of a lipase inhibition assay testing the α-chain analogs.

A series of analogs were prepared based on modifications to the alpha chain as shown in FIG. 16, generating compounds 767 and 768. While these agents had equivalent efficacy in the lipase activity assay to orlistat when fresh, agent 767 significantly retained its efficacy as a solution when left overnight. See FIG. 17.

Example 5. Inhibition of Free Fatty Acid (FFA) Generation, Toxicity, and Efficacy in Inhibiting Recombinant Human Pancreatic Tri-Acyl Glycerol Lipase [hPNLIP], Pancreatic Lipase Related Protein 2 (hPLRP2) and Carboxyester Lipase (hCEL)

Figure 18A:
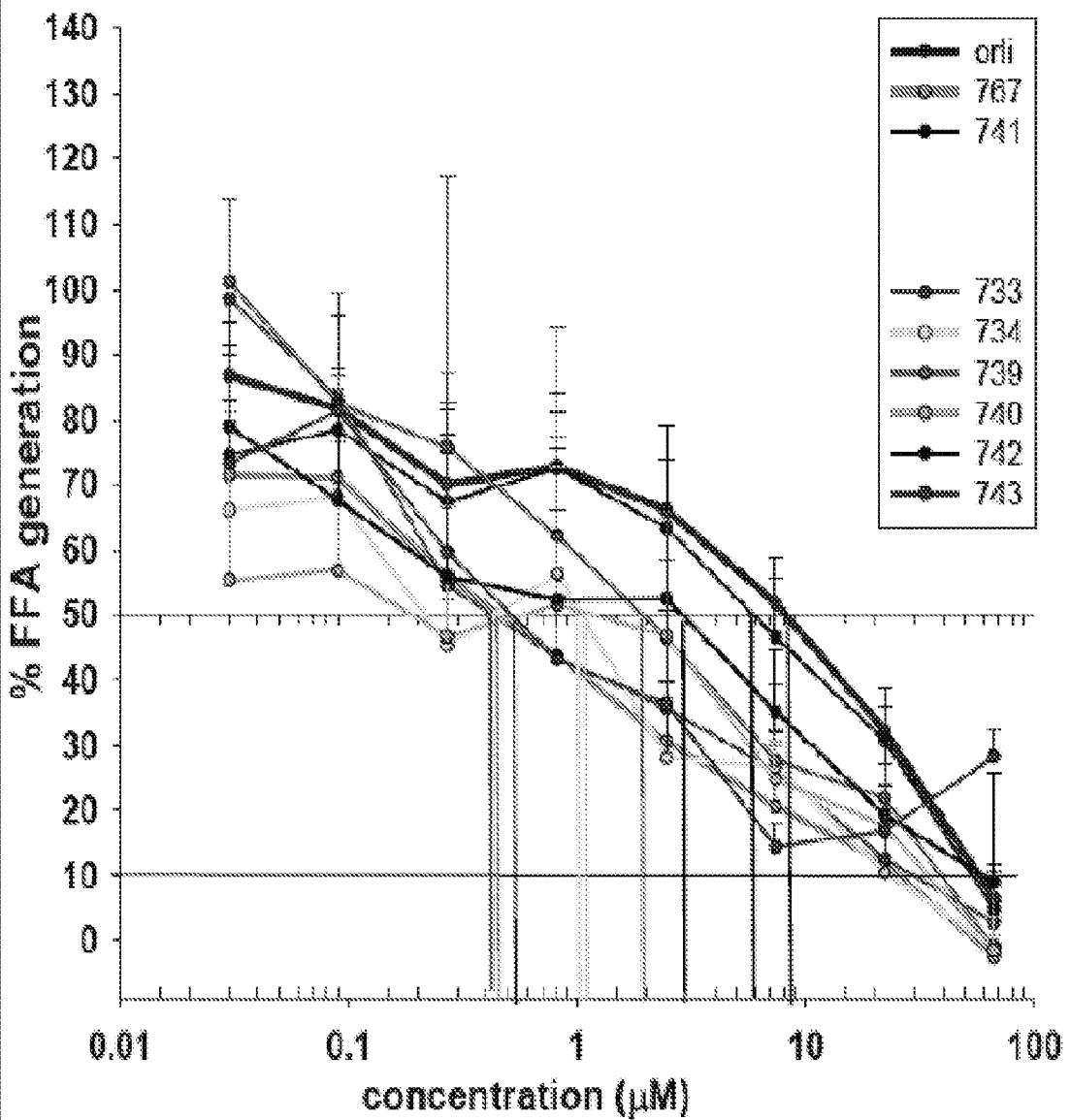
FIG. 18A provides the results of freshly prepared solutions of the compounds while FIG. 18B provides the results of solutions stored overnight.
Figure 18B:
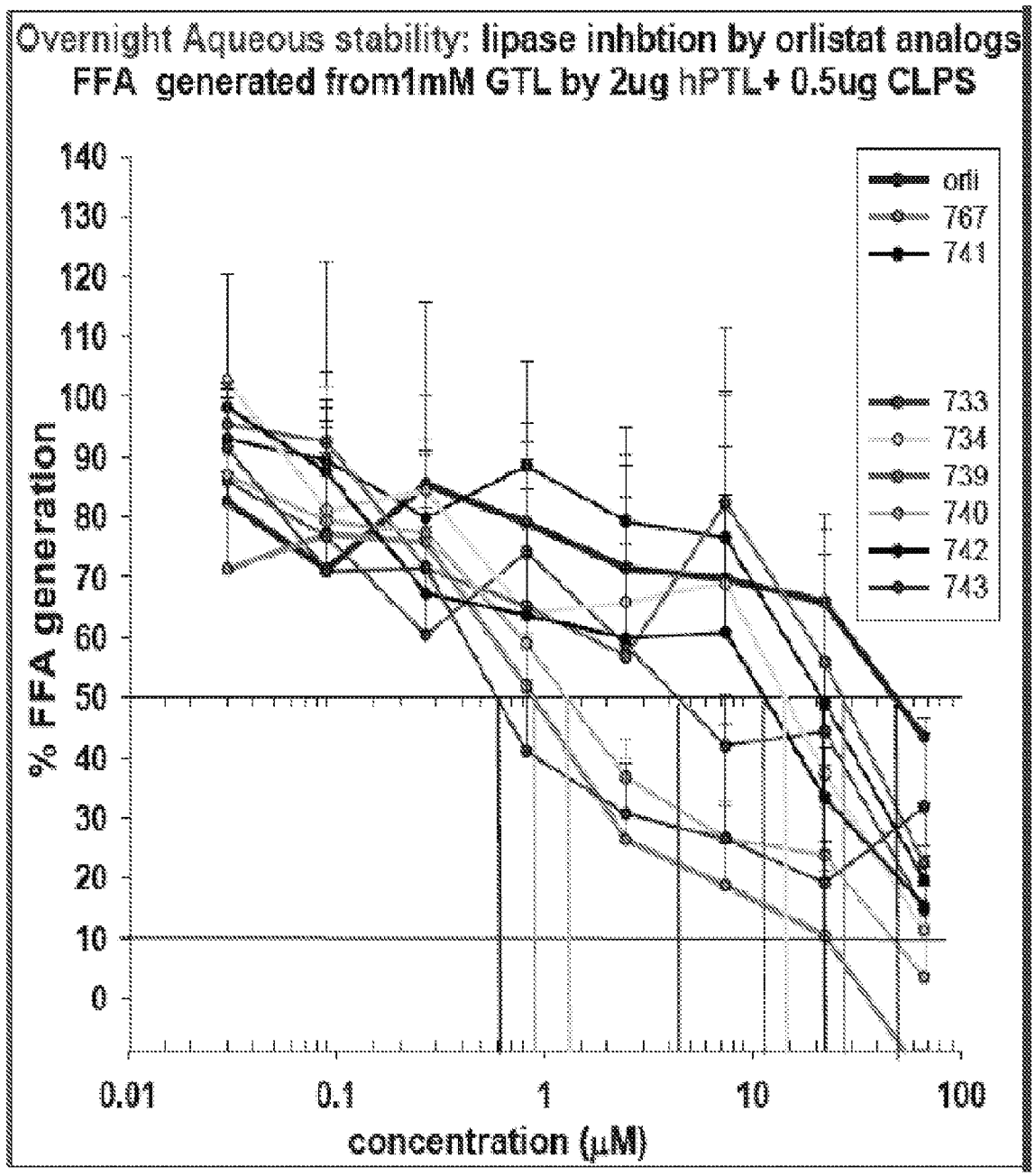
FIG. 18 provides line graphs showing the results of an assay exploring % free fatty acid (FFA) generation.

The efficacy of a selection of the prepared analogs was explored to determine their ability to inhibit free fatty acid (FFA) generation from recombinant human lipases while retaining stability. To test these features, the analogs were dissolved in ethanol (200 mM stock) and further diluted to a 600 micromolar (0.3% ethanol) working stock in PBS. The agents were incubated with the recombinant enzymes in serial ⅓ dilutions spanning a range of 200 to 0.3 micromolar for 30 minutes, and then added to the substrate 1 mM glyceryl trilinoleate (GTL) in PBS, pH 7.4 along with cofactor colipase (CLPS; 0.5 mcg/ml). As seen in FIG. 18, agents 767, 733, 734, 740 and 743 had $IC_{50s}$ against recombinant human pancreatic tri-acyl glycerol lipase [PNLIP; hPTL, in the presence of colipase (CLPS)] that were 50× lower than orlistat or 741, while retaining an $IC_{50}$<2 micromolar when stored overnight. In particular, compounds 767 and 740 displayed the best stability.

Toxicity studies of the relevant compounds were also performed using by diluting the original ethanol stock 200 mM into the incubation medium for acinar cells (HEPES buffer, pH 7.4, as described by Navina et al) 600 micromolar stock solutions of the compounds in 0.3% ethanol in PBS. These were added to acinar cells at ⅓ dilutions starting at 200 micromolar. Mouse pancreatic acinar ATP levels and LDH leakage were measured over 4 hours and compared to control. Any number positive over control indicates % injury greater than control acini. Agent 743 (See FIG. 8B), and 733 were, however, toxic to acinar cells, causing a drop in ATP and inducing LDH leakage (see FIG. 19) at concentrations in the 20-200 micromolar range—concentrations relevant to in vivo use.

Figure 20A:
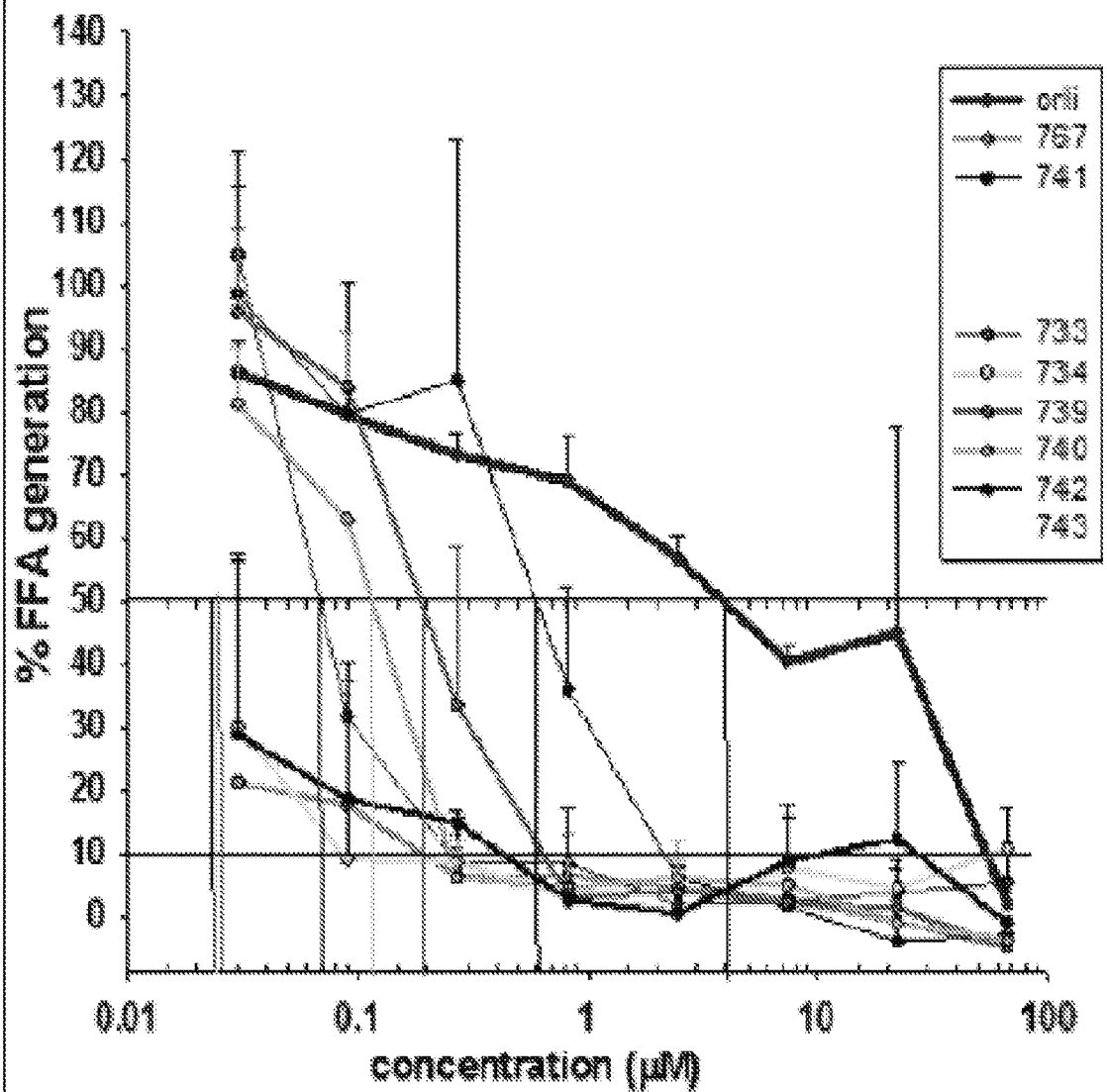
FIG. 20A provides the results with hPLRP2 lipase while FIG. 20B provides the results with hCEL lipase.
Figure 20B:
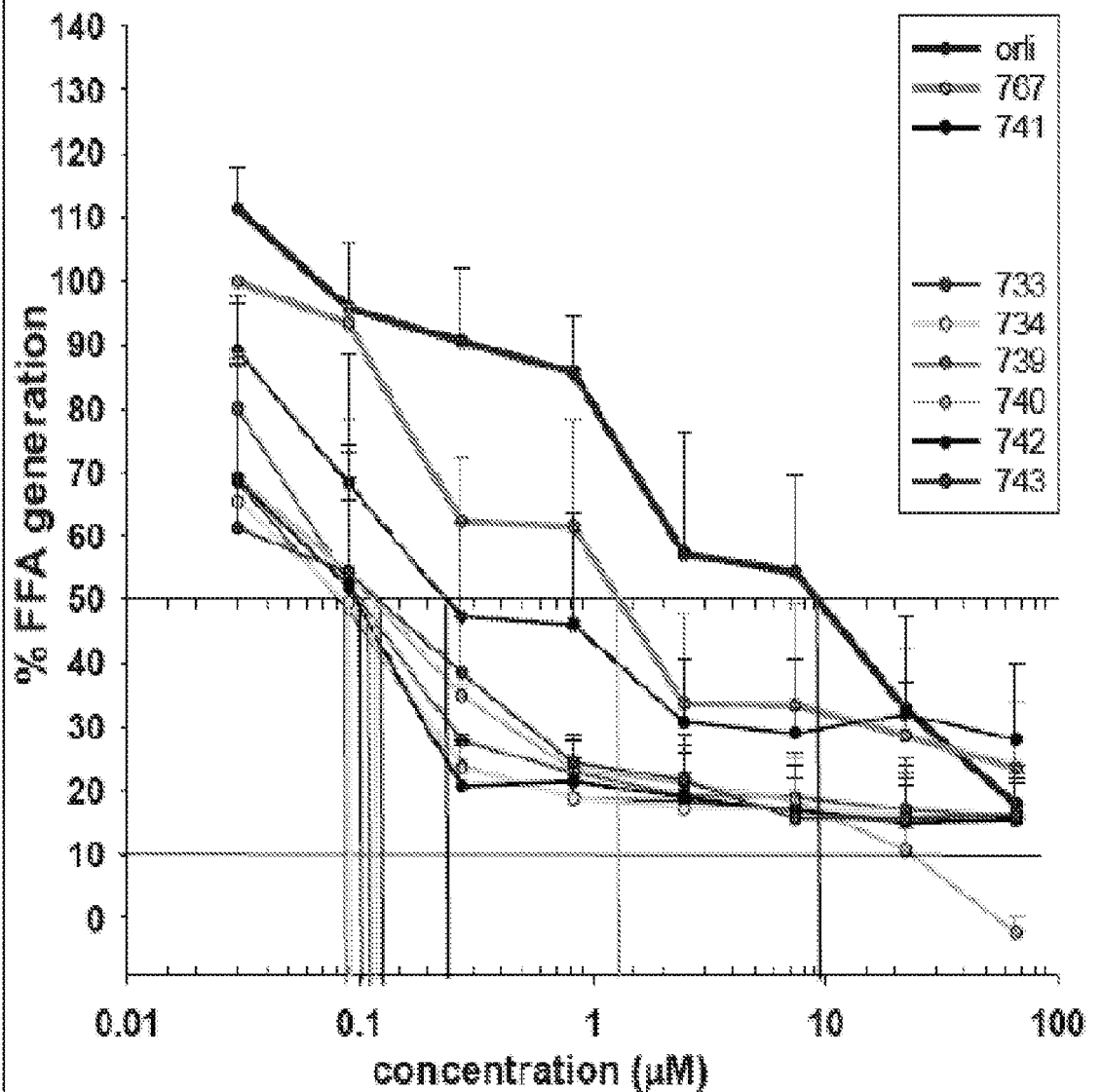
FIG. 20 provides line graphs showing the results of an assay exploring % FFA generation.
Figure 28:
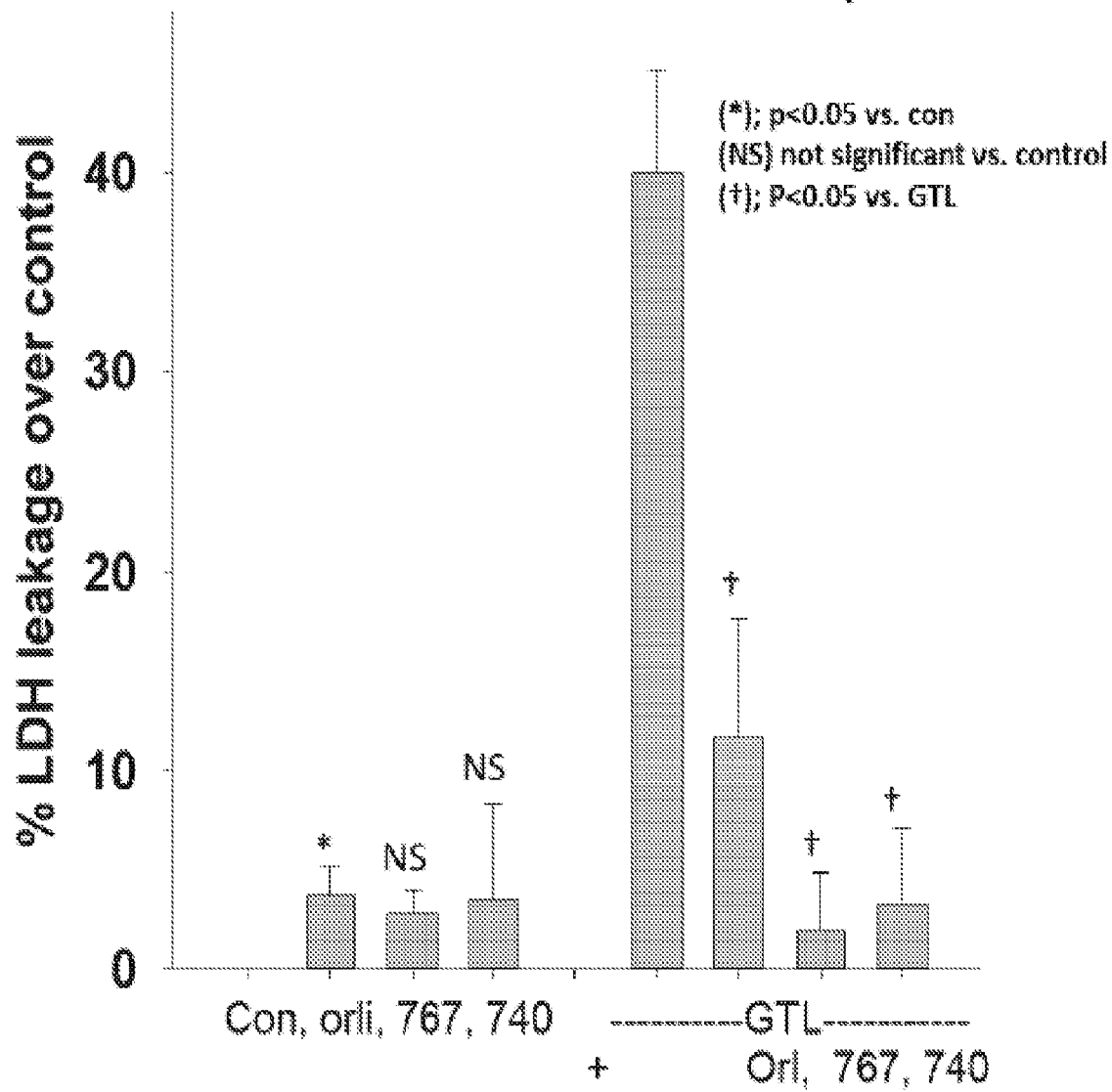
FIG. 28 shows efficacy of 10 mM agents in reducing LDH leakage from acinar cells incubated with 600 mM GTL

These compounds were further tested for efficacy in reducing recombinant human pancreatic lipase related protein 2 (hPLRP2) and carboxyester lipase (hCEL) as shown in FIG. 20. These lipases form 15-30% of pancreatic lipases. Agents 740, 734 and 767 again exhibited $IC_{50s}$ of 2 micromolars or less. The relative potency and toxicities are summarized in the table in FIG. 21. Noting this, along with the strengths of 767, i.e., a) the higher efficacy against mouse pancreatic lysates (FIGS. 7 and 17), b) higher potency against the most prevalent lipase (hPTL) (FIG. 18), c) better stability in aqueous media (FIGS. 17 and 18), and d) lower toxicity (FIG. 19), compound 767 was elected to proceed on to in vivo studies. Furthermore, Agents 740 and 767 at 10 micromolar were less toxic and more efficacious in reducing GTL induced acinar injury than orlistat (FIG. 28)

Example 6. In Vivo Studies of Compound 767

The goal of this in vivo study was to learn if the severity of lethal pancreatitis could be reduced in mice when compound 767 is administered as a single therapeutic dose, and whether the compound could avoid the limitations of orlistat, e.g., repeated high dosing and hypertriglyceridemia. See FIG. 22.

Compound 767 or orlistat was dissolved as 1 mg/10 microliter ethanol, which was diluted to 400 microliters with saline (final concentration 2.5% ethanol). Genetically obese male ob/ob mice (50-60 gm) were used and baseline tail vein blood draw was collected for serum lipase, triglycerides, and BUN (blood urea nitrogen). The time line is shown as in FIG. 23A. Severe pancreatitis was induced by implanting an alzet pump subcutaneously containing 2.5 mg/ml caerulein, which was administered at a dose of 50 mc/kg/hr. Six hours later a tail vein sample (50 microliters) was tested for serum lipase to verify an increase>3 fold basal. As seen in FIG. 23B, this was achieved (P=0.003).

The agents were then administered as an intraperitoneal dose (20 mg/kg single dose [n=8 for 767 or orlistat n=7]. Animals were given saline IP 1 mL BID, vitals were monitored daily focusing on severity (Temperature for fever or hypothermia and Pulse distention for shock). These are respectively part of SIRS and revised Atlanta criteria for severity (Classification of acute pancreatitis—2012: revision of the Atlanta classification and definitions by international consensus. Gut 2013, 62(1):102-111). tail vein samples were collected for severity parameters (Serum BUN, serum calcium and total white blood cell count) which are a part of Ranson's and Glasgow criteria) and triglycerides. Animals were sacrificed if they were moribund.

Figure 24:
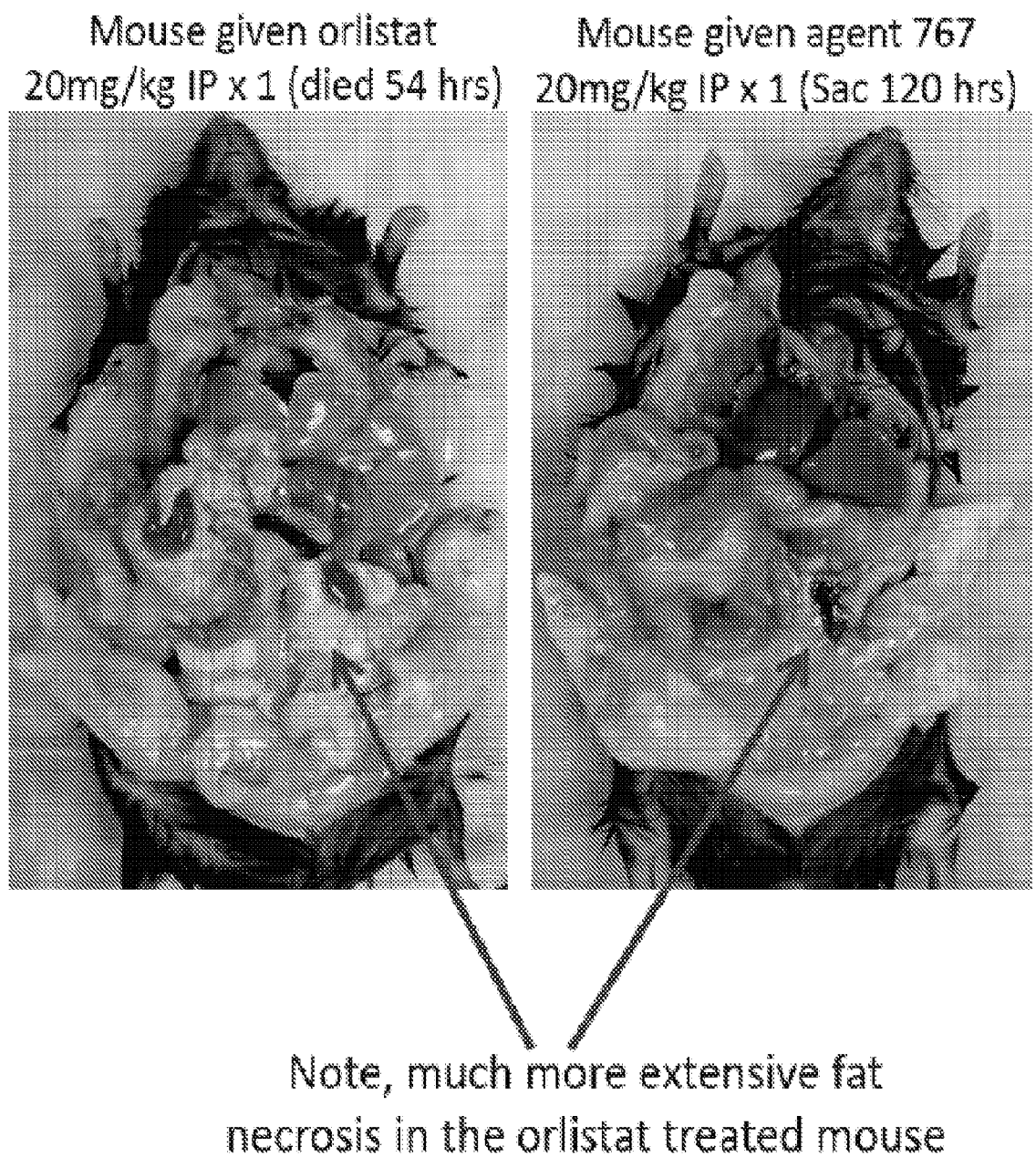

As can be seen in FIG. 23, in vivo all untreated mice developed renal failure (BUN 85±18 mg/dl) FIG. 23C, hypocalcemia (serum calcium 4.9±0.2 mg/dl) FIG. 23D, SIRS FIG. 23E, shock FIG. 23F and 100% mortality. FIG. 23G. 767 was more efficacious than orlistat in normalizing BUN (peak 18.5±0.9 vs. orlistat 50±4.4 mg/dl, p<0.05) FIG. 23C, serum calcium (8.8±1.0 mg/dl vs. 4.2±0.3 mg/dl, p<0.05) FIG. 23D, UFAs (2.4±0.4 mM vs. 5.4±0.9 mM), preventing shock (PD: 290±20 μm vs. 171±21 μm, p<0.05) FIG. 23F, leucopenia (in 0/8 mice vs. 4/7 mice, p<0.03, see FIG. 25), hypothermia (94.1±0.8 vs. 86±0.9° F., p<0.01; FIG. 23E) and improving 5 day survival (8/8 vs. 2/7, p<0.01) FIG. 23G. There was 8/8 (meantime 44 hours) mortality in the vehicle group, 5/7 mortality in the orlistat group. The gross appearance with the two agents is compared in FIG. 24. As can be seen there is much more extensive fat necrosis in the orlistat treated animal. This protection from agent 767 was achieved without the hypertriglyceridemia associated with the dosing needed for orlistat to be protective (FIG. 25). The results are summarized in the table in FIG. 25.

Example 7. FFA Generation in a Medium of P. acnes

Figure 26:
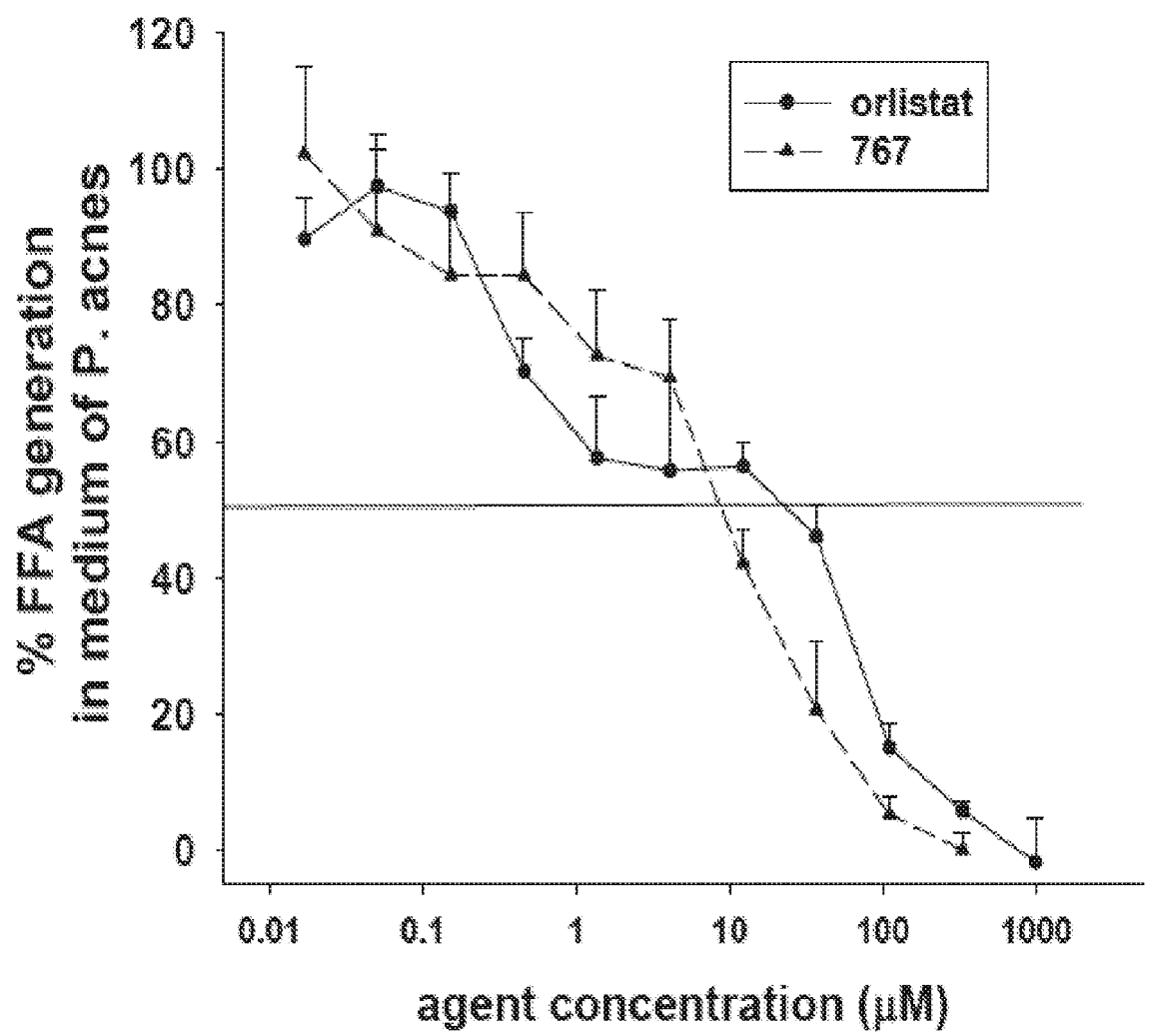
FIG. 26 provides a line graph showing % FFA generation in a medium of *P. acnes*.
Figure 27:
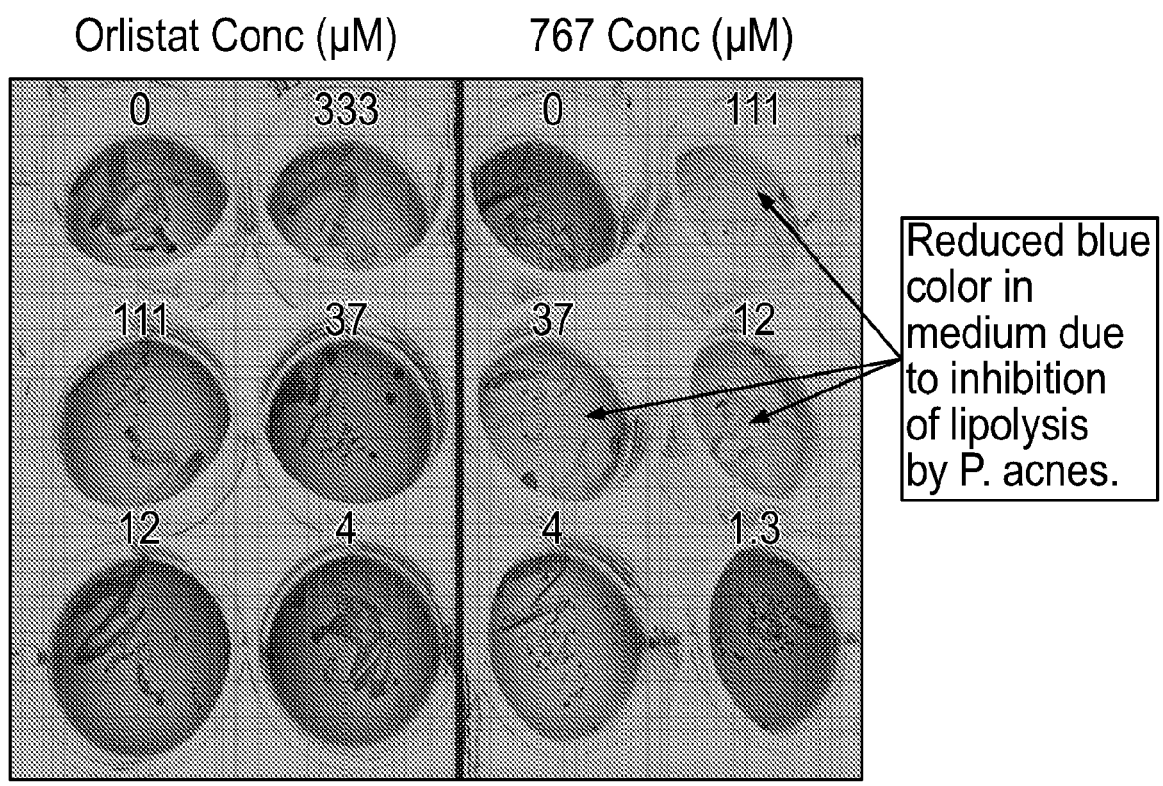
FIG. 27 provides pictures of spirit blue agar inoculated with *P. acnes* and exposed to both orlistat and compound 767.

The lipolysis by P. acnes was inhibited by 767 (FIG. 26 and FIG. 27).

P. acnes BROTH Culture:

For medium, 2.0 g of Casein hydrolysate enzymatic digest (Cat #12855, Affymetrix Inc, Ohio, USA), 1.0 g of Yeast extract (Cat #61180-5000, Acros organics, New Jersey, USA) and 0.03 g of Victoria Blue B (Cat #sc-216055, Santa Crutz Biotechnology Inc, California, USA) were dissolved completely in 200 ml of double distilled water with mild heating. The mixed solution was sterilized by autoclaving at 15 lbs pressure (121° C.) for 15 min. The autoclaved solution allowed to cool down to 50° C., then 6 ml of emulsified lipase substrate slowly added with continuous stirring to get an even distribution and stored at 4° C. for P. acnes culture.

Lipase substrate preparation: Lipase substrate was prepared by mixing 200 μl of Tween 80 (Cat #P4780, Sigma, St louis, USA) in 100 ml of warm double distilled water and 25 ml of Cotton seeds oil (Cat #C0145, Spectrum chemical, California, USA). The mixture was agitated vigorously followed by sonication (10 sec pulse×5 times) to get an emulsion.

*P. acnes* culture-expansion medium, storage conditions, size of inoculum used in medium.

A small part of lyophilized *Propionibacterium acnes* (Strain VPI0389, ATCC) was added to the medium and allowed to grow at 37° C. for 48 h in a BD GasPak EZ standard incubation container (Cat #260671, Beckton Dickinson, MD, USA) with two anaerobe Sachets (Cat #260683, Beckton Dickinson, MD, USA) which maintained the anaerobic condition within the container. After 48 h of culture, bacterial count was measured by turbidity (OD600 nm) method. Amount of secreted lipase and produced FFA were measure in the culture supernatant.

For *P. acnes* storage, cultured bacteria in 1.5 ml autoclaved eppendorf microfuge (1 ml/microfuge) was span down at 5000 rpm for 5 min, removed the spent medium, pelleted bacteria was resuspended in 15% glycerol contained *P. acnes* culture medium (1 ml/microfuge) without substrate and stored at −80° C. for future use.

For further *P acnes* culture, one aliquoted *P acnes* stock was taken out from −80° C. and thawed in ice. Almost 30 µl of *P acnes* stock (1×10⁶/30 µl) was added into 1 ml of culture medium with lipase substrate in each 2 ml Eppendorf microfuge and incubated at 37° C. for 48 h in anaerobic condition.

Efficacy Testing or Lipase Inhibitors Against *P. acnes*:

Orlistat or agent 767 (stocks 200 mM in ethanol) added at the indicated concentrations at the beginning of the incubations. At the end of the incubation period, a portion of the well mixed medium was removed, and free fatty acid generation using the HR Series NEFA-HR(2) kit from Wako Diagnostics (Richmond Va.).

*P. acnes* Agar Culture

Spirit blue agar: Supplier, catalog #. Preparation, storage. Culture inoculum size, culture conditions.

For plate preparation, 3.215 g of Spirit blue agar (Cat #M445, HiMedia Laboratories Pvt Ltd, Mumbai, India) dissolved in 100 ml of double distilled water, autoclaved, allowed to cool to 55° C., added 3 ml of warm lipase substrate and mixed well. In warm condition, the mixture was poured into tissue culture plates (6 well, 12 well plates) in aseptically. The solidified agar plates were wrapped with parafilm and kept at 37° C. overnight to confirm no contamination. The extra plates were kept at 4° C. freezer for future use. Either thawed *P. acnes* −80° C. stock was spread out (30 µl/well) in 6 well/12 well plates or inoculated throughout the well by means of inoculating loops. Then the plates were kept at 37° C. in BD GasPak EZ chamber with one anaerobe sachets and waited for 5-7 days to see the bacterial colonies. These were then visualized and photographed on a trans illuminator.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

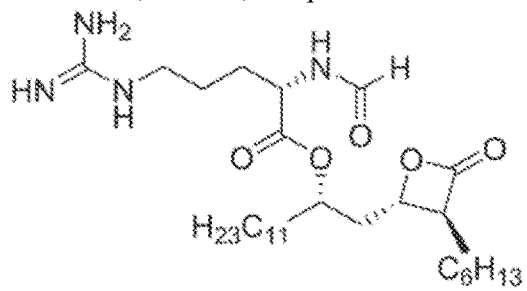

What is claimed is:

1. A compound selected from the group consisting of:

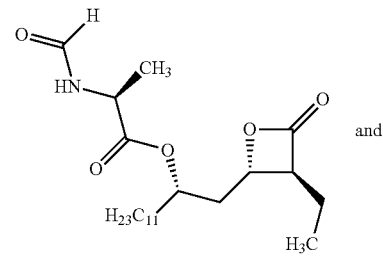

and

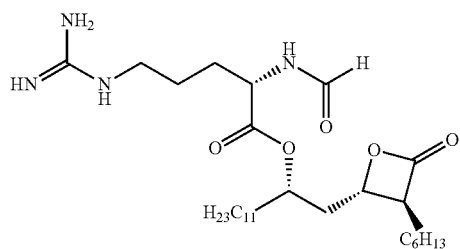

or a pharmaceutically acceptable salt thereof.

2. The compound of claim 1, wherein the compound is:

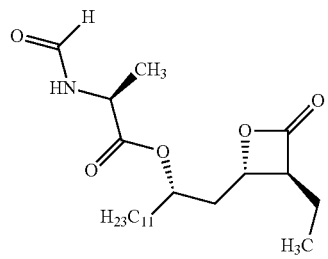

or a pharmaceutically acceptable salt thereof.

3. The compound of claim 1, wherein the compound is:

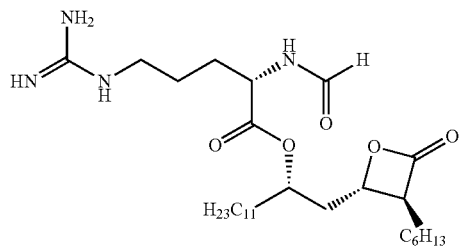

or a pharmaceutically acceptable salt thereof.

4. A pharmaceutical composition comprising a compound of claim 1, or a pharmaceutically acceptable salt thereof, and a pharmaceutically acceptable excipient.

5. A method of treating acute pancreatitis in a subject in need thereof, the method comprising administering to the subject a therapeutically effective amount of a compound selected from the group consisting of:

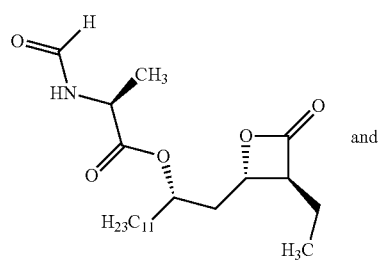

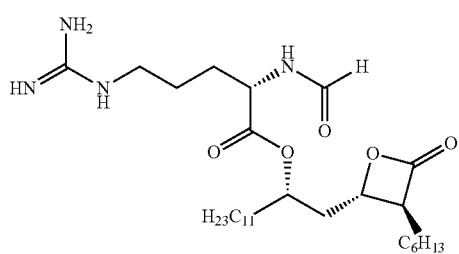

or a pharmaceutically acceptable salt thereof.

6. The method of claim 5, wherein the acute pancreatitis is severe.

7. The method of claim 5, wherein the acute pancreatitis is downgraded from severe to mild following administration.

8. The method of claim 5, wherein the subject is obese.

9. A method of treating acne in a subject in need thereof, the method comprising administering to the subject a therapeutically effective amount of a compound selected from the group consisting of:

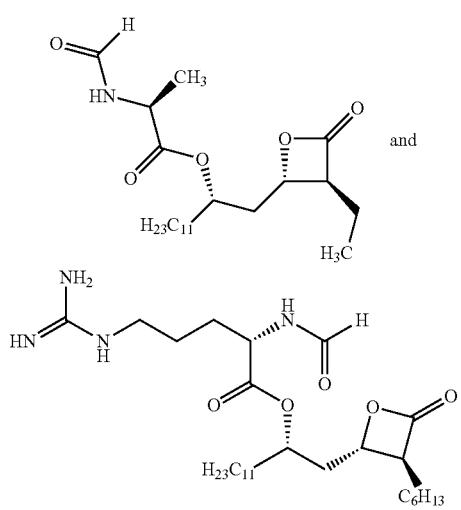

or a pharmaceutically acceptable salt thereof.

10. A method of treating sepsis in a subject in need thereof, the method comprising administering to the subject a therapeutically effective amount of a compound selected from the group consisting of:

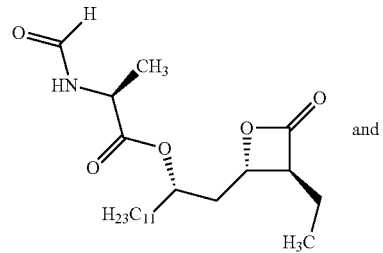

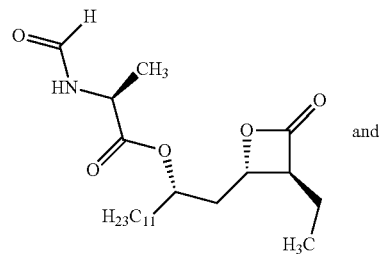

or a pharmaceutically acceptable salt thereof.

11. The method of claim 10, wherein the sepsis is culture negative sepsis.

12. A method of treating burns in a subject in need thereof, the method comprising administering to the subject a therapeutically effective amount of a compound selected from the group consisting of:

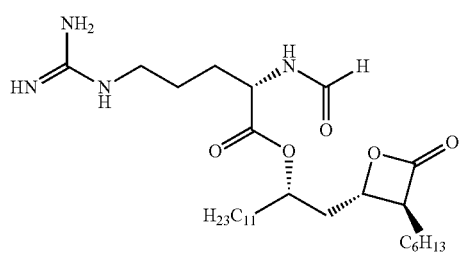

or a pharmaceutically acceptable salt thereof.

13. A method for treating infections in a subject in need thereof, the method comprising administering to the subject a therapeutically effective amount of a compound selected from the group consisting of:

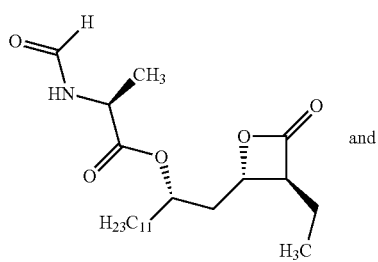

and

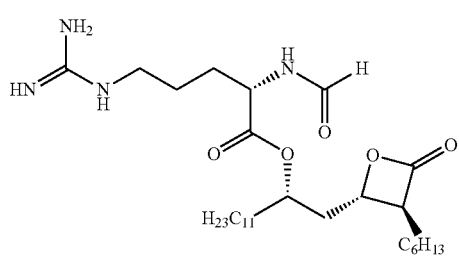

or a pharmaceutically acceptable salt thereof, wherein the infection is caused by one or more organisms selected from the group consisting of *P. auregenosa, S. aureus, B. subtilis*, and *B. cepecia*.

14. The method of claim 5, wherein the compound is:

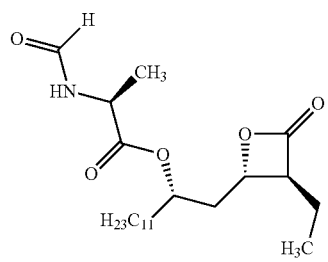

or a pharmaceutically acceptable salt thereof.

15. The method of claim 5, wherein the compound is:

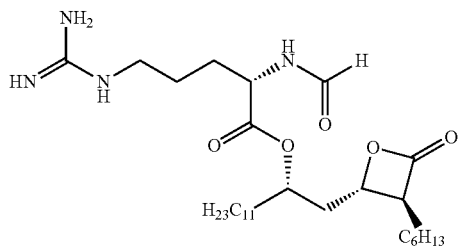

or a pharmaceutically acceptable salt thereof.

* * * * *

UNITED STATES PATENT AND TRADEMARK OFFICE
CERTIFICATE OF CORRECTION

PATENT NO. : 11,339,126 B2
APPLICATION NO. : 16/629842
DATED : May 24, 2022
INVENTOR(S) : Singh et al.

Page 1 of 2

It is certified that error appears in the above-identified patent and that said Letters Patent is hereby corrected as shown below:

On the Title Page

(57) Abstract, Page 2, Column 1: Please delete the first formula and replace with the following:

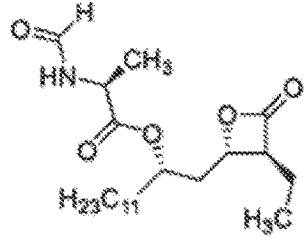

In the Specification

Column 1, Lines 56-66: Please delete the formula and replace with the following:

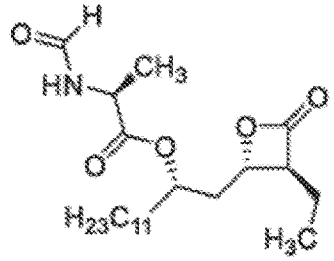

Signed and Sealed this
Twenty-fifth Day of October, 2022

Katherine Kelly Vidal
*Director of the United States Patent and Trademark Office*

CERTIFICATE OF CORRECTION (continued)
U.S. Pat. No. 11,339,126 B2

Column 2, Lines 16-26: Please delete the formula and replace with the following:

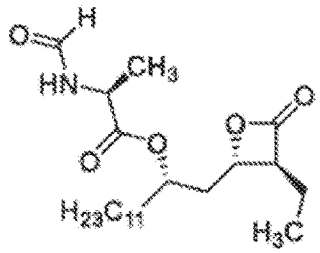

Column 3, Lines 15-25: Please delete the formula and replace with the following:

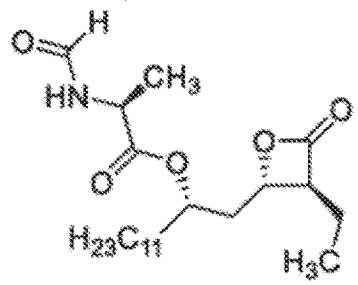

Column 13, Table 1, compound #740: Please delete the formula and replace with the following: